(12) United States Patent
Blythe et al.

(10) Patent No.: US 8,460,537 B2
(45) Date of Patent: Jun. 11, 2013

(54) METHODS FOR DETERMINING AN ANALYTE CONCENTRATION USING SIGNAL PROCESSING ALGORITHMS

(75) Inventors: Stephen Patrick Blythe, Inverness (GB); Marco F Cardosi, Croy (GB); Leanne Mills, Milton of Leys (GB); Manuel Alvarez-Icaza, Inverness (GB); Emma Vanessa Jayne Day, Culbokie Duncanston (GB); Richard Michael Day, Duncanston (GB); Christopher Philip Leach, Inverness (GB)

(73) Assignee: LifeScan Scotland Limited (GB)

( * ) Notice: Subject to any disclaimer, the term of this patent is extended or adjusted under 35 U.S.C. 154(b) by 565 days.

(21) Appl. No.: 12/553,976

(22) Filed: Sep. 3, 2009
(Under 37 CFR 1.47)

(65) Prior Publication Data

US 2011/0005941 A1    Jan. 13, 2011

Related U.S. Application Data

(63) Continuation of application No. 12/305,359, filed as application No. PCT/GB2007/003781 on Oct. 5, 2007, now abandoned.

(60) Provisional application No. 60/850,107, filed on Oct. 5, 2006.

(51) Int. Cl.
*G01F 1/64* (2006.01)
*G01N 17/00* (2006.01)
*G01N 27/26* (2006.01)

(52) U.S. Cl.
USPC .......................................... 205/775; 205/792

(58) Field of Classification Search
USPC ..... 205/775, 792; 204/403.14, 403.04; 702/25
See application file for complete search history.

(56) References Cited

U.S. PATENT DOCUMENTS

| 5,312,590 | A  | 5/1994 | Gunasingham |
| 5,653,918 | A  | 8/1997 | Towlson |
| 5,708,247 | A  | 1/1998 | McAleer et al. |
| 6,046,051 | A  | 4/2000 | Jina |
| 6,179,979 | B1 | 1/2001 | Hodges et al. |

(Continued)

FOREIGN PATENT DOCUMENTS

| AU | 2006200073 A1 | 2/2006 |
| EP | 0928967 A     | 7/1999 |

(Continued)

OTHER PUBLICATIONS

L. Chen, et al., "*Bioinorganic composites for enzyme electrodes*", vol. 73, No. 13, pp. 2862-2868, XP002463785, Jul. 1, 2001.

(Continued)

*Primary Examiner* — Luan Van
*Assistant Examiner* — Louis Rufo

(57) ABSTRACT

A method for determining an analyte concentration in blood is described that reduces the effects of hematocrit using a test strip attached to a test meter. The test strip includes a working electrode and a reference electrode. The test meter applies a test voltage between the working electrode and the reference electrode. After a user applies a blood sample containing an analyte onto the test strip, the test meter measures a plurality of test currents for a test time interval.

16 Claims, 15 Drawing Sheets

U.S. PATENT DOCUMENTS

| | | |
|---|---|---|
| 6,241,862 B1 | 6/2001 | McAleer et al. |
| 6,448,794 B1 | 9/2002 | Cheng et al. |
| 7,112,265 B1 | 9/2006 | McAleer |
| 2003/0116447 A1 | 6/2003 | Surridge et al. |
| 2003/0143113 A2 | 7/2003 | Yuzhakov et al. |
| 2003/0153820 A1* | 8/2003 | Berner et al. .............. 600/345 |
| 2003/0217918 A1 | 11/2003 | Davies et al. |
| 2003/0235817 A1* | 12/2003 | Bartkowiak et al. ............ 435/5 |
| 2004/0259264 A1* | 12/2004 | Morita et al. ................ 436/149 |
| 2004/0260511 A1 | 12/2004 | Burke et al. |
| 2005/0096409 A1 | 5/2005 | Davies et al. |

FOREIGN PATENT DOCUMENTS

| | | | |
|---|---|---|---|
| EP | 1156324 A | 11/2001 | |
| EP | 1318399 A | 6/2003 | |
| EP | 1426757 A | 6/2004 | |
| EP | 1447660 A | 8/2004 | |
| EP | 1467206 A | 10/2004 | |
| EP | 1496354 A | 1/2005 | |
| EP | 1775587 A | 4/2007 | |
| EP | 1839571 A | 10/2007 | |
| EP | 1840219 A | 10/2007 | |
| WO | WO 01/67099 A1 | 9/2001 | |
| WO | WO 01/73124 A2 | 10/2001 | |
| WO | WO 02/49507 A1 | 6/2002 | |
| WO | WO 03/097860 A | 11/2003 | |
| WO | WO 2004/039600 A2 | 5/2004 | |
| WO | WO 2004/039897 A2 | 5/2004 | |
| WO | WO 2004/040005 A1 | 5/2004 | |
| WO | WO 2004/040285 A1 | 5/2004 | |
| WO | WO 2004/040287 A1 | 5/2004 | |
| WO | WO 2004/040290 A1 | 5/2004 | |
| WO | WO 2004/040948 A1 | 5/2004 | |
| WO | WO 2005/045414 A | 5/2005 | |
| WO | WO 2006/057722 A | 6/2006 | |
| WO | WO 2006/072089 A | 7/2006 | |

OTHER PUBLICATIONS

PCT Search Report, PCT patent application No. PCT/GB2007/003791, dated Oct. 4, 2008, 4 pages.

PCT Search Report, PCT patent application No. PCT/GB2007/003770, dated Jan. 16, 2008, 3 pages.

PCT Search Report, PCT patent application No. PCT/GB2007/003781, dated Mar. 25, 2008, 3 pages.

PCT Search Report, PCT patent application No. PCT/GB2007/003790, dated Jan. 25, 2008, 2 pages.

PCT Search Report, PCT patent application No. PCT/GB2007/003772, dated Jan. 21, 2008, 3 pages.

* cited by examiner

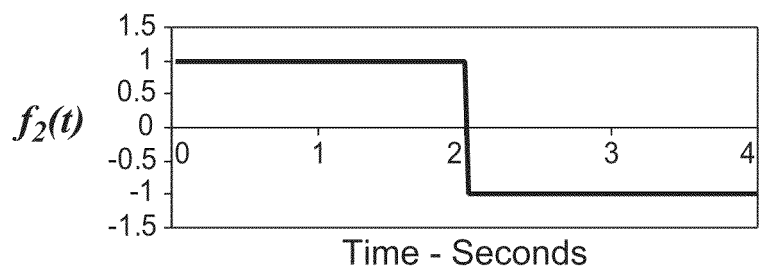
FIG. 16 $f_2(t)$
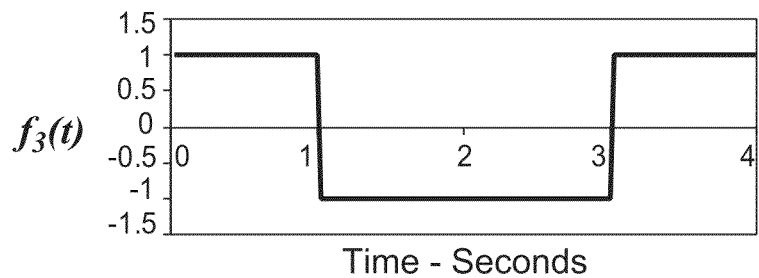
FIG. 17 $f_3(t)$
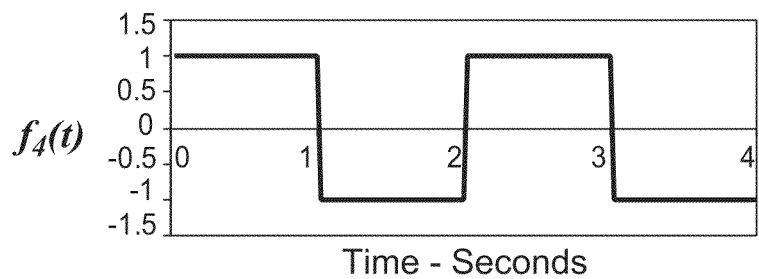
FIG. 18 $f_4(t)$
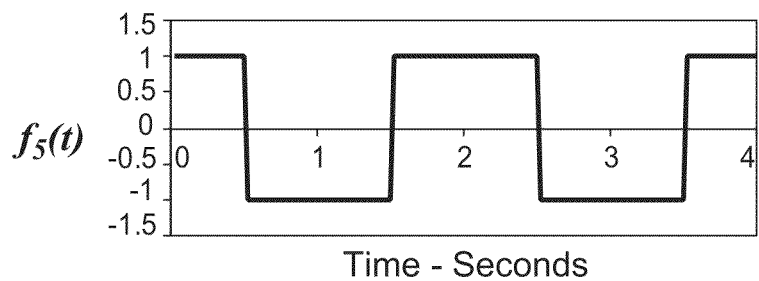
FIG. 19 $f_5(t)$
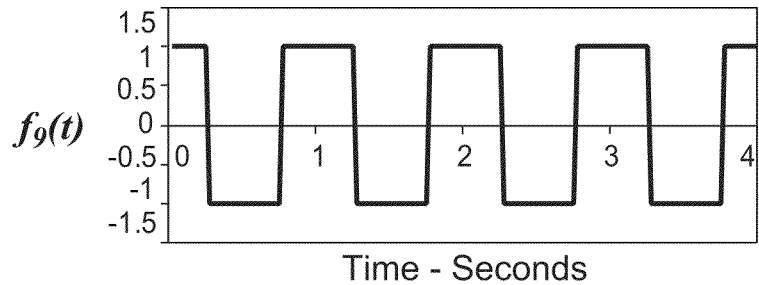
FIG. 20 $f_9(t)$

METHODS FOR DETERMINING AN ANALYTE CONCENTRATION USING SIGNAL PROCESSING ALGORITHMS

PRIORITY

This application is a continuation application and claims the benefit of priority under 35 USC §§ 119 and 120 to U.S. patent application Ser. No. 12/305,359, International Application filing date Oct. 5, 2007, which claims priority from International Application number PCT/GB2007/003781, filed Oct. 5, 2007, which claims priority from provisional application Ser. No. 60/850,107 filed on Oct. 5, 2006, in which all applications are incorporated by reference in their entirety herein.

DESCRIPTION OF THE RELATED ART

Electrochemical glucose test strips, such as those used in the OneTouch®Ultra® whole blood testing kit, which is available from LifeScan, Inc., are designed to measure the concentration of glucose in a blood sample from patients with diabetes. The measurement of glucose is based upon the specific oxidation of glucose by the enzyme glucose oxidase (GO). The reactions which may occur in a glucose test strip are summarized below in Equations 1 and 2.

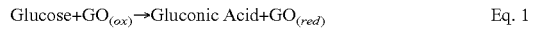
$$\text{Glucose} + GO_{(ox)} \rightarrow \text{Gluconic Acid} + GO_{(red)} \quad \text{Eq. 1}$$

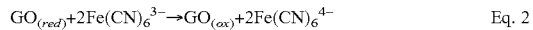
$$GO_{(red)} + 2Fe(CN)_6^{3-} \rightarrow GO_{(ox)} + 2Fe(CN)_6^{4-} \quad \text{Eq. 2}$$

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the reaction in Equation 1, the oxidized enzyme $GO_{(ox)}$ is converted to its reduced state, which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ (referred to as either the oxidized mediator or ferricyanide) as illustrated in Equation 2. During the re-generation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test voltage applied between two electrodes, a test current may be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test current, resulting from the re-oxidation of reduced mediator, and glucose concentration. In particular, the transfer of electrons across the electrical interface results in the flow of a test current (2 moles of electrons for every mole of glucose that is oxidized). The test current resulting from the introduction of glucose may, therefore, be referred to as a glucose current.

Because it can be very important to know the concentration of glucose in blood, particularly in people with diabetes, test meters have been developed using the principals set forth above to enable the average person to sample and test their blood for determining their glucose concentration at any given time. The glucose current generated is detected by the test meter and converted into a glucose concentration reading using an algorithm that relates the test current to a glucose concentration via a simple mathematical formula. In general, the test meter works in conjunction with a disposable test strip that includes a sample receiving chamber and at least two electrodes disposed within the sample receiving chamber in addition to the enzyme (e.g. glucose oxidase) and the mediator (e.g. ferricyanide). In use, the user pricks their finger or other convenient site to induce bleeding and introduces a blood sample to the sample receiving chamber, thus starting the chemical reaction set forth above.

In electrochemical terms, the function of the meter is two fold. Firstly, it provides a polarizing voltage (approximately 400 mV in the case of OneTouch® Ultra®) that polarizes the electrical interface and allows current flow at the carbon working electrode surface. Secondly, it measures the current that flows in the external circuit between the anode (working electrode) and the cathode (reference electrode). The test meter may, therefore be considered to be a simple electrochemical system that operates in a two-electrode mode although, in practice, third and, even fourth electrodes may be used to facilitate the measurement of glucose and/or perform other functions in the test meter.

In most situations, the equation set forth above is considered to be a sufficient approximation of the chemical reaction taking place on the test strip and the test meter outputting a sufficiently accurate representation of the glucose content of the blood sample. However, under certain circumstances and for certain purposes, it may be advantageous to improve the accuracy of the measurement. For example, blood samples having a high hematocrit level or low hematocrit level may cause a glucose measurement to be inaccurate.

A hematocrit level represents a percentage of the volume occupied by red blood cells. In general, a high hematocrit blood sample is more viscous (up to about 10 centipoise at 70% hematocrit) than a low hematocrit blood sample (about 3 centipoise at 20% hematocrit). In addition, a high hematocrit blood sample has a higher oxygen content than a low hematocrit blood because of the concomitant increase in hemoglobin, which is a carrier for oxygen. Thus, the hematocrit level can influence the viscosity and oxygen content of blood. As will be later described, both viscosity and oxygen content may change the magnitude of the glucose current and in turn cause the glucose concentration to be inaccurate.

A high viscosity sample (i.e., high hematocrit blood sample) can cause the test current to decrease for a variety of factors such as a decrease in 1) the dissolution rate of enzyme and/or mediator, 2) the enzyme reaction rate, and 3) the diffusion of a reduced mediator towards the working electrode. A decrease in current that is not based on a decrease in glucose concentration can potentially cause an inaccurate glucose concentration to be measured.

A slower dissolution rate of the reagent layer can slow down the enzymatic reaction as illustrated in Equations 1 and 2 because the oxidized enzyme $GO_{(ox)}$ must dissolve first before it can react with glucose. Similarly, ferricyanide (Fe$(CN)_6^{3-}$) must dissolve first before it can react with reduced enzyme $GO_{(red)}$. If the undissolved oxidized enzyme $GO_{(ox)}$ cannot oxidize glucose, then the reduced enzyme $GO_{(red)}$ cannot produce the reduced mediator $Fe(CN)_6^{4-}$ needed to generate the test current.

Further, oxidized enzyme $GO_{(ox)}$ will react with glucose and oxidized mediator $Fe(CN)_6^{3-}$ more slowly if it is in a high viscosity sample as opposed to a low viscosity sample. The slower reaction rate with high viscosity samples is ascribed to an overall decrease in mass diffusion. Both oxidized enzyme $GO_{(ox)}$ and glucose must collide and interact together for the reaction to occur as illustrated in Equation 1. The ability of oxidized enzyme $GO_{(ox)}$ and glucose to collide and interact together is slowed down when they are in a viscous sample.

Yet further, reduced mediator $Fe(CN)_6^{4-}$ will diffuse to the working electrode slower when dissolved in a high viscosity sample. Because the test current is typically limited by the diffusion of reduced mediator $Fe(CN)_6^{4-}$ to the working electrode, a high viscosity sample will also attenuate the test current. In summary, there are several factors which cause the test current to decrease when the sample has an increased viscosity.

A high oxygen content may also cause a decrease in the test current. The reduced enzyme $(GO_{(red)})$ can reduce oxygen $(O_2)$ to hydrogen peroxide as illustrated be Equation 3.

$$GO_{(red)} + O_2 \rightarrow GO_{(ox)} + H_2O_2 \qquad \text{Eq. 3}$$

As noted earlier, the reduced enzyme $GO_{(red)}$ can also reduce ferricyanide $(Fe(CN)_6^{3-})$ to ferrocyanide $(Fe(CN)_6^{4-})$ as illustrated in Equation 2. Thus, oxygen can compete with ferricyanide for reacting with the reduced enzyme $(GO_{(red)})$. In other words, the occurrence of the reaction in Equation 3 will likely cause a decrease in the rate of the reaction in Equation 2. Because of such a competition between ferricyanide and oxygen, a higher oxygen content will cause less ferrocyanide to be produced. In turn, a decrease in ferrocyanide would cause a decrease in the magnitude of the test current. Therefore, a high oxygen content blood sample can potentially decrease the test current and affect the accuracy of the glucose measurement.

As such, there is great interest in the development of methods reducing the effects of hematocrit on a glucose measurement. In certain protocols, a pre-cast blood filtering membrane which is separate from the reagent layer has been employed to remove red blood cells and thereby reduce the hematocrit effect. The pre-cast blood filtering membrane which is separated from the reagent layer can be deposed on the working electrode. The use of a discrete pre-cast blood filtering membrane is unsatisfactory in that it requires a more complex test strip, increased sample volume, and increased testing time. The blood filtering membrane retains a certain amount of blood that does not contact the working electrodes causing a need for a larger blood sample. In addition, a finite amount of time is needed for the blood to be filtered by the membrane causing an increase in the overall test times. Thus, it would be advantageous to reduce the effects of hematocrit without using a pre-cast blood filtering membrane which is separate from the reagent layer.

In the prior art, the hematocrit effect may be reduced by applying multiple test voltages such as, for example, a sinusoidal test voltage. However, applying a sinusoidal test voltages results in a more complex and expensive test meter. Further, the test meter needs to measure the test currents accurately and precisely at pre-determined time intervals. The electronic components can be expensive and complicated for a test meter to accurately and precisely apply multiple test voltages.

Applicants recognize that it would be advantageous to implement a system, which uses a test meter that applies only one test voltage, and a test strip, that does not use a pre-cast membrane, for reducing the effects of hematocrit. Such a system should be inexpensive and simple to make. More particularly, applicants recognize that it would be advantageous to develop an algorithm that mathematically processes the collected test current using one test voltage such that an accurate glucose concentration can be determined which reduces the effects of hematocrit.

In a prior art method, a glucose concentration may be determined using an algorithm that samples only a small proportion of the measured test current which may be less accurate at extreme hematocrit levels (e.g., 0% or 70%) than an algorithm which uses a larger proportion of the measured test currents. For example, an "end current" algorithm, which calculates an average current value for five test current values at around 5 seconds, may be less accurate than an algorithm which uses all or substantially all of the test current values. Thus, applicants realize that there is a need to develop an algorithm that uses a greater proportion of the test current values for substantially reducing the effects of hematocrit.

SUMMARY OF INVENTION

A method for determining an analyte concentration in blood is described that reduces the effects of hematocrit using a test strip attached to a test meter. The test strip includes a working electrode and a reference electrode. The test meter applies a test voltage between the working electrode and the reference electrode. After a user applies a blood sample containing an analyte onto the test strip, the test meter measures a plurality of test currents for a test time interval. The test meter calculates an analyte correlation value (Y) using the equations as illustrated below, $$Y = \sum_{t=t_{F1}}^{t_{L1}} I(h, G, t)q(t) + \sum_{t=t_{F2}}^{t_{L2}} I(h, G, t)q(t) + \sum_{t=t_{F3}}^{t_{L3}} I(h, G, t)q(t)$$

where I is the test current value in units of microamperes; h is hematocrit in units of a fraction; G is glucose concentration in units of mg/dL; t is time in units of seconds; $t_{F1}$ is a starting point of a first pre-determined time interval; $t_{L1}$ comprises an ending time point of a first pre-determined time interval; $t_{F2}$ is a starting point of a second pre-determined time interval; $t_{L2}$ is an ending point of a second pre-determined time interval; $t_{F3}$ is a starting point of a third pre-determined time interval; $t_{L3}$ includes an ending point of a third pre-determined time interval; q(t) is a correction function where, in one embodiment of the invention, the correction function is +1 between the starting point $t_{F1}$ and the ending point $t_{L1}$ for the first pre-determined time interval, −1 between the starting point $t_{F2}$ and the ending point $t_{L2}$ for the second pre-determined time interval, and +1 between the starting point $t_{F3}$ and the ending point $t_{L3}$ for the third pre-determined time interval. An accurate glucose concentration may be determined based on the analyte correlation value (Y).

The starting and ending points of the first, second, and third pre-determined. time intervals (i.e., $t_{F1}$, $t_{L1}$, $t_{F2}$, $t_{L2}$, $t_{F3}$, and $t_{L3}$) and the correction function q(t) are determined and optimized such that the analyte correlation value (Y) has little to no dependence on the hematocrit level in blood. Once the terms $t_{F1}$, $t_{L1}$, $t_{F2}$, $t_{L2}$, $t_{F3}$, $t_{L3}$, and q(t) have been determined, they can be stored on a memory portion of a test meter.

In one embodiment of this invention, an error minimization function S may be used to define the terms $t_{F1}$, $t_{L1}$, $t_{F2}$, $t_{L2}$, $t_{F3}$, and $t_{L3}$. The error minimization function S may include a background sensitivity function a(t), glucose sensitivity function b(t), and hematocrit sensitivity function c(t). An example of an error minimization function S is shown below.

$$S = [\int a(t)c(t)q(t)dt]^2 + [\int b(t)c(t)q(t)dt]^2 \approx 0$$

In one embodiment, a sum of a duration of a first pre-determined time interval and of the third pre-determined time interval does not equal the second pre-determined time interval. However, in another embodiment, a sum of a duration of the first pre-determined time interval and of the third pre-determined time interval equals the second pre-determined time interval, which is a form of a Walsh-Hadamard transform.

The analyte correlation value (Y) may be calculated during the test time interval as opposed to performing the calculation once the test time interval has elapsed. The test meter can calculate a glucose concentration more efficiently by performing the calculations during the test time interval enabling the glucose concentration to be displayed more quickly once the test time has elapsed.

As another embodiment of this invention, the method for determining the ending point for the first pre-determined time interval may be refined to include a determination of the maximum peak time from the plurality of test currents. The ending point for the first pre-determined time interval may be determined by multiplying the maximum peak time times a calibration factor, where the calibration factor ranges from about 0.5 to about less than one.

A test strip, suitable for use with the method embodiment of reducing the effects of hematocrit, may include a reagent layer disposed over the working electrode. The reagent layer may be formed from a formulation which includes an enzyme, a ruthenium hexamine mediator, and a buffer. In particular, the ruthenium hexamine may have a concentration range from about 15% to about 20% (weight/volume). The enzyme may be either glucose oxidase or glucose dehydrogenase. The buffer may be phosphate, citrate, or citraconate. For an embodiment using phosphate buffer, the pH may be about 7.

In one embodiment, the reagent layer may further include a filler having hydrophilic and hydrophobic domains. The filler may be a silica which has been modified by partial surface treatment with methyl dichlorosilane. The reagent layer may be printed on the working electrode via a screen. The screen may include a plurality of interwoven threads secure to a frame. The plurality of interwoven threads may form a plurality of open rectangular spaces for allowing the formulation to pass therethrough. The plurality of interwoven threads may have a thread spacing and a thread diameter, where the thread spacing ranges from about 90 threads per centimeter to about 120 threads per centimeter and the thread diameter may range from about 30 microns to about 50 microns.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 16 is a graph of a Walsh-Hadamard transform function $f_2(t_v)$ where there are two pre-determined time intervals, for use in Equations 14 and 15, which processes the test current values for determining a glucose concentration;

FIG. 17 is a graph of a Walsh-Hadamard transform function $f_3(t_v)$ where there are three pre-determined time intervals, for use in Equations 14 and 15, which processes the test current values for determining a glucose concentration;

FIG. 18 is a graph of a Walsh-Hadamard transform function $f_4(t_v)$ where there are four pre-determined time intervals, for use in Equations 14 and 15, which processes the test current values for determining a glucose concentration;

FIG. 19 is a graph of a Walsh-Hadamard transform function $f_5(t_v)$ where there are five pre-determined time intervals, for use in Equations 14 and 15, which processes the test current values for determining a glucose concentration;

FIG. 20 is a graph of a Walsh-Hadamard transform function $f_9(t_v)$ where there are nine pre-determined time intervals, for use in Equations 14 and 15, which processes the test current values for determining a glucose concentration;

is on the x-axis and $$\frac{I(t)}{I_{ss}}$$

is on the y-axis for calculating a slope for determining the effective diffusion coefficient D using Equation 17.

DETAILED DESCRIPTION OF ILLUSTRATIVE EMBODIMENTS OF THE INVENTION

Although various embodiments of the present invention are particularly adapted to the measurement of glucose concentration in blood, it will be apparent to those skilled in the art that the methods described herein may be adapted to decrease the hematocrit effect of other systems used for the electrochemical measurement of analytes. Examples of systems that may be adapted to decrease the hematocrit effect using the method according to the present invention include electrochemical sensors used to measure the concentration of lactate, ethanol, cholesterol, amino acids, choline, hemoglobin, and fructosamine in blood.

It will be further understood that this invention is not limited to only correcting for hematocrit and can also be applicable to for correcting for other situations where variable viscosity or oxygen content samples may be observed. Blood can have a high viscosity for a variety of other reasons in addition to high hematocrit. For example, a low temperature (e.g., around 10° C.), high lipid concentration, and/or high protein concentration can also cause a blood sample to become more viscous.

The various embodiments of the invention are also applicable for reducing the effects caused by oxygen and/or viscosity of physiological fluids other than blood. For example, physiological fluids may also include plasma, serum, interstitial fluid, and a combination thereof. It should be noted that it is not uncommon for extracted interstitial fluid samples to be partially mixed with blood.

Embodiments of the present invention are directed to a method of calculating an accurate glucose concentration in blood that has a reduced effect from hematocrit. In an embodiment of this invention, a single test voltage is applied to a test strip for a test time interval. The test meter measures a plurality of test current values during the test time interval. At least a portion of the plurality of test current values are mathematically processed using an algorithm of the exemplary embodiments to reduce the effects of hematocrit and output an accurate glucose concentration. The algorithm of the exemplary embodiments can be simple to perform in that it does not require a fast microprocessor. In fact, the algorithm of the exemplary embodiments may be substantially performed using a simple microprocessor during the test time interval while the test current values are being measured, as opposed to starting the algorithm after the test time interval has elapsed.

Figure 1:
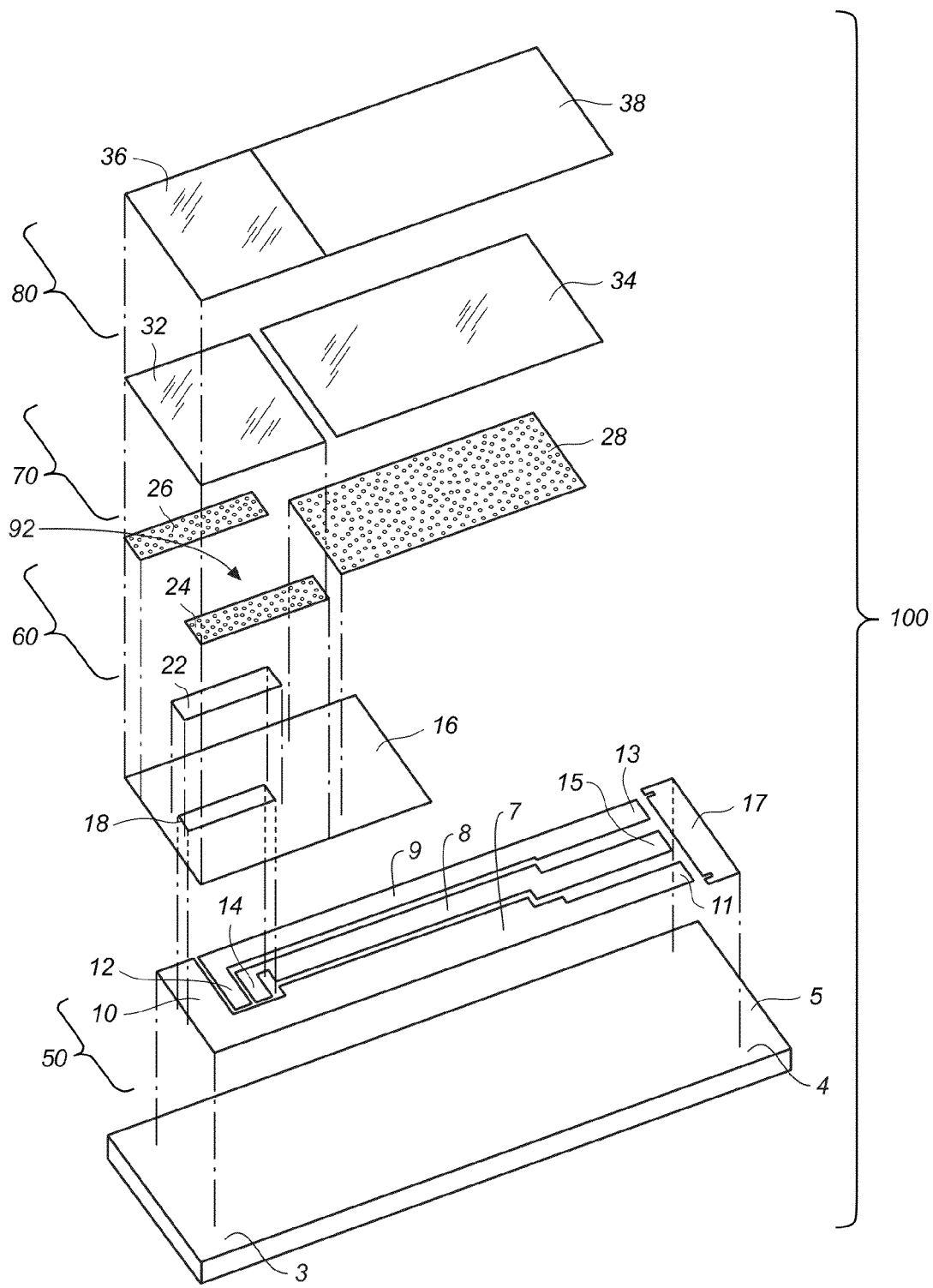
FIG. 1 illustrates a top exploded perspective view of an unassembled test strip suitable for use in the exemplary embodiments.

The following sections will describe a test strip embodiment that may be used with the proposed algorithm of the exemplary embodiments for calculating an accurate glucose concentration with a reduced hematocrit effect. FIG. 1 is an exploded perspective view of a prior art test strip 100, which includes six layers disposed on a substrate 5. These six layers may be a conductive layer 50, an insulation layer 16, a reagent layer 22, an adhesive layer 60, a hydrophilic layer 70, and a top layer 80. Test strip 100 may be manufactured in a series of steps wherein the conductive layer 50, insulation layer 16, reagent layer 22, adhesive layer 60 are sequentially deposited on substrate 5 using, for example, a screen printing process as described in U.S. Pre-Grant Publication No. US20050096409A1 and published International Application No.'s WO2004040948A1, WO2004040290A1, WO2004040287A1, WO2004040285A2, WO2004040005A1, WO2004039897A2, and WO2004039600A2. In an alternative embodiment, an ink jetting process may be used to deposit reagent layer 22 which is described in U.S. Pat. No. 6,179,979. Hydrophilic layer 70 and top layer 80 may be deposed from a roll stock and laminated onto substrate 5. Test strip 100 has a distal portion 3 and a proximal portion 4 as illustrated in FIGS. 1 and 2.

Figure 2:
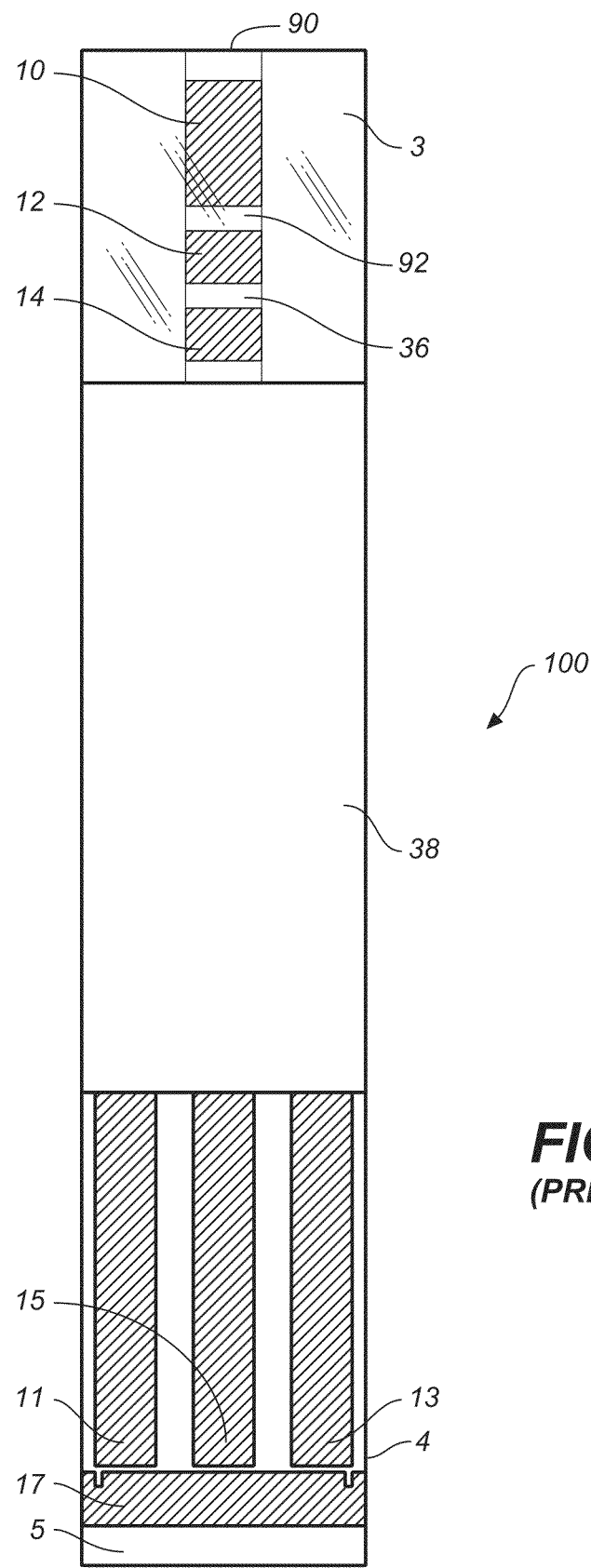
FIG. 2 illustrates a top plan view of the test strip as illustrated in FIG. 1 after it has been assembled.
Figure 3:
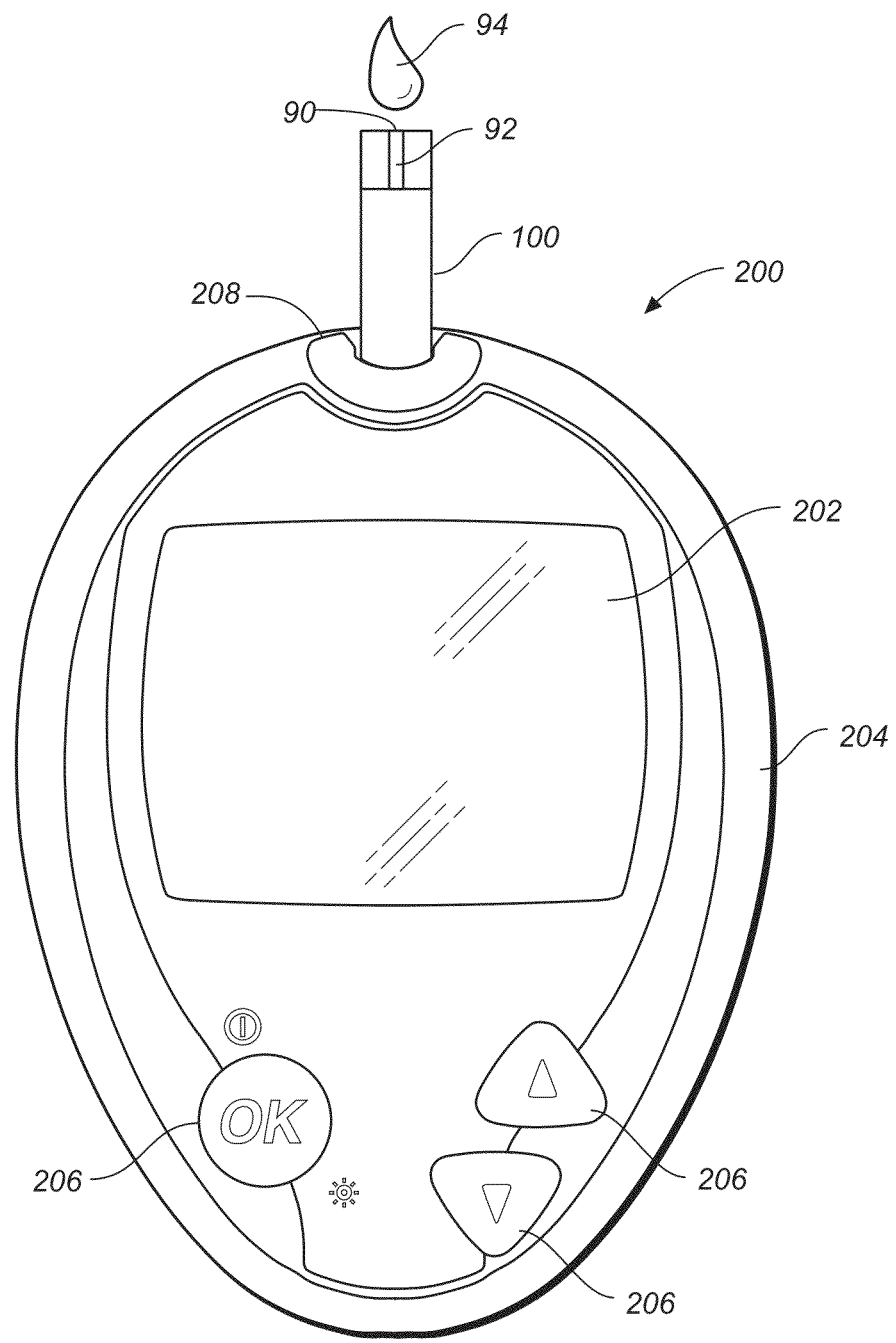
FIG. 3 illustrates a top plan view of a test meter suitable for use with the exemplary embodiments where the test meter is connected to the test strip of FIG. 1.

The fully assembled test strip 100, as illustrated in FIG. 2, includes an inlet 90 through which a blood sample may be drawn into a sample receiving chamber 92. Inlet 90 may be formed by cutting through a distal portion 3 of test strip 100. A blood sample 94 can be applied to inlet 90, as illustrated in FIG. 3, to fill a sample receiving chamber 92 so that glucose can be measured. The side edges of a first adhesive pad 24 and a second adhesive pad 26 located adjacent to reagent layer 22 each define a wall of sample receiving chamber 92. A bottom portion or "floor" of sample receiving chamber 92 includes a portion of substrate 5, conductive layer 50, and insulation layer 16. A top portion or "roof" of sample receiving chamber 92 includes distal hydrophilic portion 32.

For test strip 100, as illustrated in FIG. 1, conductive layer 50 includes a reference electrode 10, a first working electrode 12, a second working electrode 14, a first contact 13, a second contact 15, a reference contact 11, a first working electrode track 8, a second working electrode track 9, a reference electrode track 7, and a strip detection bar 17. The conductive layer may be a carbon ink such as the one described in U.S. Pat. No. 5,653,918. First contact 13, second contact 15, and reference contact 11 may be adapted to electrically connect to test meter 200. First working electrode track 8 provides an electrically continuous pathway from first working electrode 12 to first contact 13. Similarly, second working electrode track 9 provides an electrically continuous pathway from second working electrode 14 to second contact 15. Similarly, reference electrode track 7 provides an electrically continuous pathway from reference electrode 10 to reference contact 11.

In FIG. 1, insulation layer 16 includes aperture 18 which exposes a portion of reference electrode 10, first working electrode 12, and second working electrode 14 which can be wetted by a liquid sample. As an example, insulation layer 16 may be Ercon E6110-116 Jet Black Insulayer™ ink which may be purchased from Ercon, Inc (Waltham, Mass.).

Reagent layer 22 may be disposed on a portion of conductive layer 50, substrate 5, and insulation layer 16 as illustrated in FIG. 1. Reagent layer 22 may include chemicals such as an enzyme and a mediator which selectivity react with glucose. An example of an enzyme may be glucose oxidase and an example of a mediator may be ferricyanide.

Examples of enzymes suitable for use with embodiments described herein may include either glucose oxidase or glucose dehydrogenase. More specifically, the glucose dehydrogenase may have a pyrrylo-quinoline quinone co-factor (abbreviated as PQQ or may be referred to its common name which is methoxatin). Examples of mediator suitable for use in this invention may include either ferricyanide or ruthenium hexamine trichloride ([Ru$^{III}$(NH$_3$)$_6$]Cl$_3$ and may also be simply referred to as ruthenium hexamine). During the reactions as illustrated in Equations 1 and 2, a proportional amount of reduced mediator can be generated that is electrochemically measured for calculating a glucose concentration. Examples of reagent formulations or inks suitable for use in the embodiments can be found in U.S. Pat. Nos. 5,708,247 6,046,051, and 6,241,862; U.S. Pre-Grant Publication No. 20030217918A1; published international applications WO01/67099 and WO01/73124.

Reagent layer 22 may be formed from an enzyme ink or formulation which is deposited onto a conductive layer and dried. An enzyme ink or formulation typically contains a liquid, such as a buffer, for dispersing and/or dissolving materials used for the electrochemical detection of an analyte such as glucose. Buffers which may be suitable for the formulation can be phosphate, citrate and citraconate.

In an embodiment of this invention, the formulation may include a 200 mM phosphate buffer having a pH of about 7 and a ruthenium hexamine mediator concentration ranging from about 5% and greater, preferably ranging from about 10% and greater, and yet more preferably ranging from about 15% to about 20% (percentage based on weight of mediator/volume of buffer). The pH of around 7 was chosen because glucose oxidase has a sufficiently high activity at this pH when using ruthenium hexamine as a mediator. The upper range for the ruthenium hexamine concentration may be selected based on its solubility. When the enzyme ink is formulated to have greater than a 20% ruthenium hexamine concentration, solid particles of ruthenium hexamine may be present in reagent layer 22 which do not dissolve during testing. The presence of undissolved ruthenium hexamine may cause a decrease in the test strip-to-test strip precision. When the enzyme ink is formulated to have less than a 15% ruthenium hexamine concentration, the magnitude of the test current values may decrease with the concentration of ruthenium hexamine. In general, it is undesirable for the magnitude of the test current values to be dependent on the concentration of ruthenium hexamine because small changes in ruthenium hexamine concentration will cause variability in the test current values and, in turn, the strip lot-to-strip lot variability.

In an embodiment of this invention, the formulation may have an enzyme activity ranging from about 1500 units/mL to about 8000 units/mL. The enzyme activity range may be selected so that the glucose current does not depend on the level of enzyme activity in the formulation so long as the enzyme activity level is within the above stated range. The enzyme activity should be sufficiently large to ensure that the resulting glucose current will not be dependent on small variations in the enzyme activity. For instance, the glucose current will depend on the amount of enzyme activity in the formulation if the enzyme activity is less than 1500 units/mL. On the other hand, for enzyme activity levels greater than 8000 units/mL, solubility issues may arise where the glucose oxidase cannot be sufficiently dissolved in the formulation. Glucose oxidase may be commercially available from Biozyme Laboratories International Limited (San Diego, Calif., U.S.A.). The glucose oxidase may have an enzyme activity of about 250 units/mg using where the enzyme activity units are based on an o-dianisidine assay at pH 7 and 25° C.

An enzyme ink which contains a filler having both hydrophobic and hydrophilic domains may be deposed onto the working electrode using a screen printing process. An example of a filler may be a silica such as, for example, Cab-o-Sil TS 610 which is commercially available from Cabot Inc., Boston, Mass. Typically, a screen may be in the form of a rectangular frame which secures a plurality of interwoven threads. The plurality of interwoven threads form a plurality of open rectangular spaces for allowing enzyme ink to pass therethrough. The density and the size of the open spaces influence the amount of enzyme ink which becomes deposited on the conductive layer. Characteristics of the interwoven threads which influence the deposition of the enzyme ink are thread spacing and thread diameter. The thread spacing may range from about 90 threads per centimeter to about 120 threads per centimeter. The thread diameter may range from about 30 microns to about 50 microns. More specifically, in an embodiment of this invention, a screen suitable for screen printing an enzyme ink having ruthenium hexamine and glucose oxidase may have a thread spacing of about 120 threads per centimeter and a thread diameter of about 34 microns.

For test strip 100, adhesive layer 60 includes first adhesive pad 24, second adhesive pad 26, and third adhesive pad 28 as illustrated in FIG. 1. Adhesive layer 60 may include a water based acrylic copolymer pressure sensitive adhesive which is commercially available from Tape Specialties LTD which is located in Tring, Herts, United Kingdom (part#A6435). Adhesive layer 60 is deposed on a portion of insulation layer 16, conductive layer 50, and substrate 5. Adhesive layer 60 binds hydrophilic layer 70 to test strip 100.

Hydrophilic layer 70 includes a distal hydrophilic portion 32 and proximal hydrophilic portion 34. Hydrophilic layer 70 may be a polyester having one hydrophilic surface such as an anti-fog coating which is commercially available from 3M.

For test strip 100, top layer 80 includes a clear portion 36 and opaque portion 38 as illustrated in FIG. 1. Top layer 80 is disposed on and adhered to hydrophilic layer 70. Top layer 80 may be a polyester. It should be noted that the clear portion 36 substantially overlaps distal hydrophilic portion 32 which allows a user to visually confirm that the sample receiving chamber 92 may be sufficiently filled. Opaque portion 38 helps the user observe a high degree of contrast between a colored fluid such as, for example, blood within the sample receiving chamber 92 and the opaque portion 38 of top layer 80.

FIG. 3 illustrates a test meter 200 suitable for connecting to test strip 100. Test meter 200 includes a display 202, a housing 204, a plurality of user interface buttons 206, and a strip port connector 208. Test meter 200 further includes electronic circuitry within housing 204 such as a memory 210, a microprocessor 212, electronic components for applying a test voltage, and also for measuring a plurality of test current values (see 104 and 106 in FIG. 4). Proximal portion 4 of test strip 100 may be inserted into strip port connector 208. Display 202 may output a glucose concentration and also may be used to show a user interface for prompting a user on how to perform a test. The plurality of user interface buttons 206 allow a user to operate test meter 200 by navigating through the user interface software.

Figure 4:
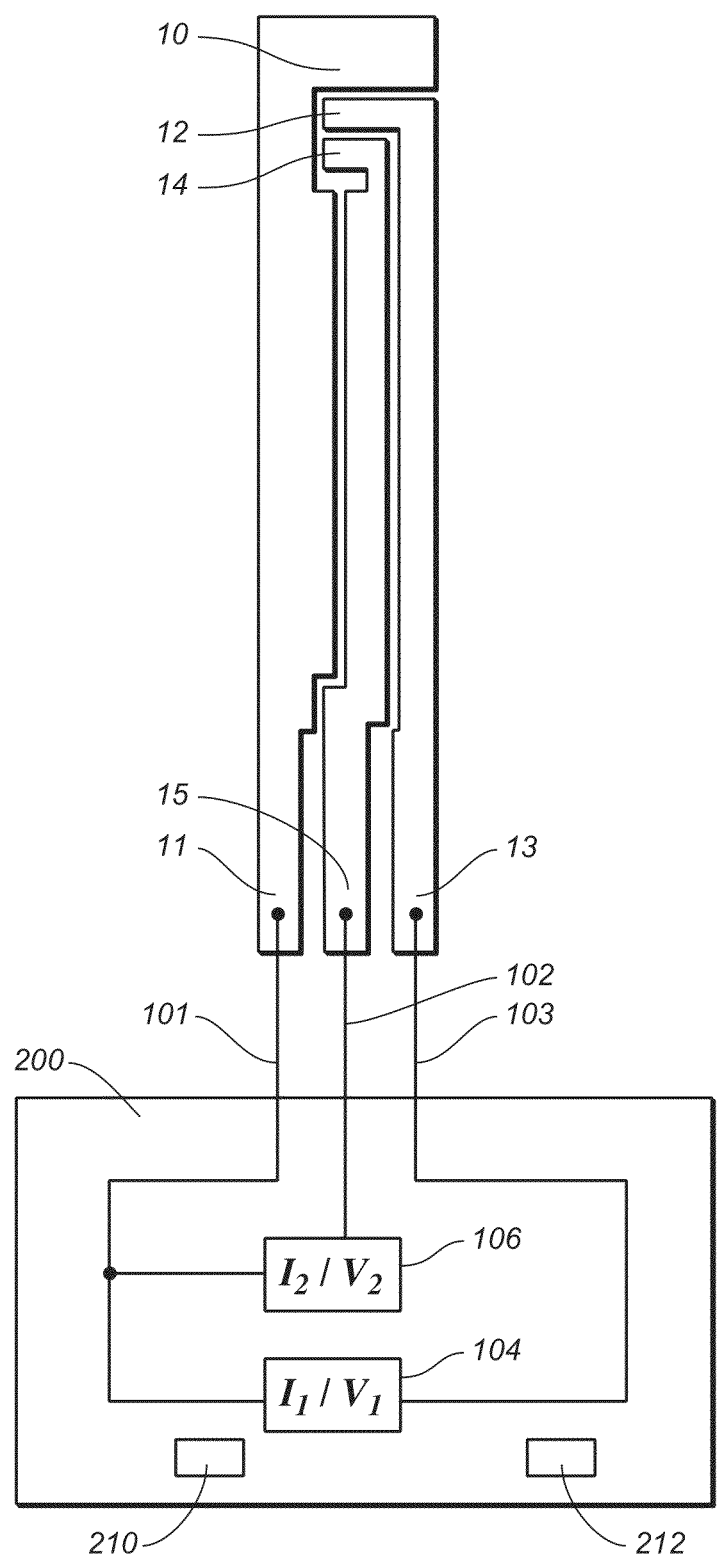
FIG. 4 illustrates a simplified schematic view of the test meter of FIG. 3 forming an electrical connection with the test strip of FIG. 1.

FIG. 4 shows a simplified schematic of test meter 200 interfacing with test strip 100. Test meter 200 includes a first connector 103, second connector 102, and a reference connector 101 which respectively form an electrical connection to first contact 13, second contact 15, and reference contact 11. The three aforementioned connectors are part of strip port connector 208. When performing a test, a first test voltage source 104 applies a first test voltage $V_1$ between first working electrode 12 and reference electrode 10. As a result of first test voltage $V_1$, test meter 200 may then measure a first test current $I_1$. In a similar manner, second test voltage source 106 applies a second test voltage $V_2$ between second working electrode 14 and reference electrode 10. As a result of second test voltage $V_2$, test meter 200 may then measure a second test current $I_2$. In an embodiment of this invention, first test voltage $V_1$ and second test voltage $V_2$ may be about equal allowing a glucose measurement to be performed twice where a first measurement is performed with first working electrode 12 and a second measurement is performed with second working electrode 14. The use of two glucose measurements can increase accuracy by averaging the two results together. For simplifying the description of the following sections, the algorithms for determining an accurate glucose concentration will be described for only one working electrode and reference electrode. It should be apparent to one skilled in the art, that the invention should not be limited to one working electrode and reference electrode, but that multiple working electrodes can also be applied to the exemplary embodiments.

Figure 5:
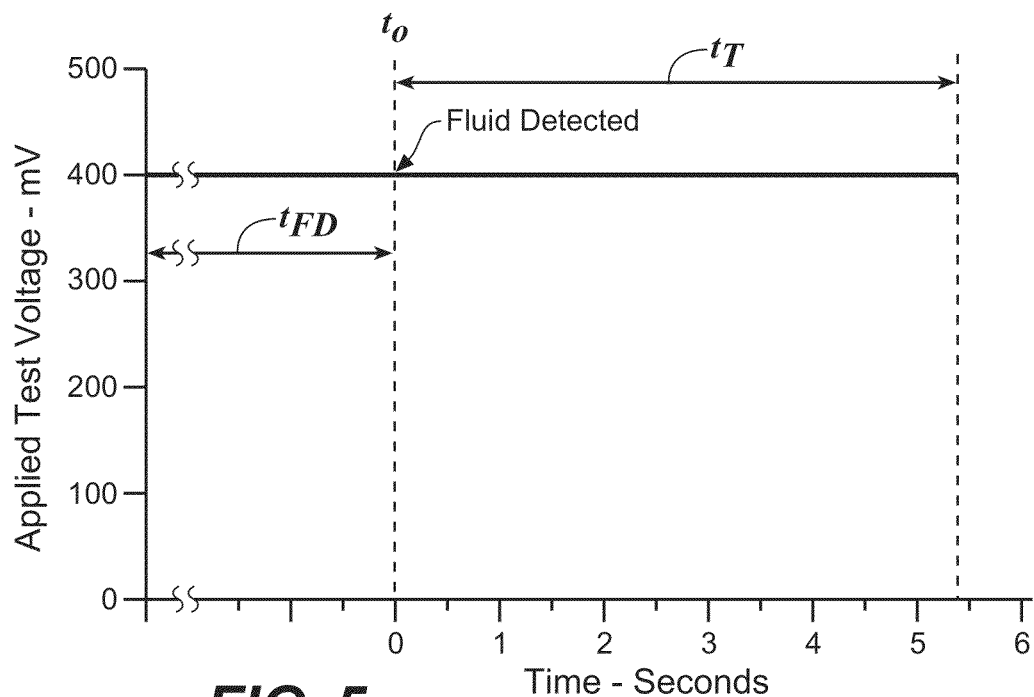
FIG. 5 is a graph illustrating the application of an applied test voltage, from the test meter of FIG. 3, to the test strip of FIG. 1, for a test time interval $t_T$ for generating a test current which can be used for calculating an analyte concentration in accordance with the exemplary embodiments.

FIG. 5 is a chart showing a test voltage that would be applied by test meter 200 to test strip 100 for a test time interval $t_T$ which starts when physiological fluid is detected by test strip 100. In FIG. 5, the test voltage shown is 400 mV. As illustrated in FIG. 5, before the physiological fluid is applied, test meter 200 is in a fluid detection mode in which a fluid detection voltage may be 400 mV. It will be apparent to one skilled in the art that the test voltage and the fluid detection voltage can be different. In FIG. 5, the test meter is in a fluid detection mode during fluid detection time interval $t_{FD}$ prior to the detection of physiological fluid at time $t_0$. In the fluid detection mode, test meter 200 determines when a fluid is applied to inlet 90 and pulled into sample receiving chamber 92 such that the fluid wets both first working electrode 12 and reference electrode 10. Note that first working electrode 12 and reference electrode 10 are effectively short-circuited when the physiological fluid contiguously covers both first working electrode 12 and reference electrode 10. Once test meter 200 recognizes that the physiological fluid has been applied because of, for example, a sufficient increase in the measured test current, test meter 200 assigns a zero second marker at time $t_0$ and starts the test time interval $t_T$. For example, as shown in FIG. 5, test time interval $t_T$ may be about 5.4 seconds. Upon the completion of the test time interval $t_T$, the test voltage is removed.

In general, it is desirable to use a test voltage which is more positive than a redox voltage of the mediator used in the test strip. In particular, the test voltage should exceed the redox voltage by an amount sufficient to ensure that the resulting test current will not be dependent on small variations in the test voltage. Note that a redox voltage describes a mediator's intrinsic affinity to accept or donate electrons when sufficiently close to an electrode having a nominal voltage. When a test voltage is sufficiently positive with respect to the mediator's redox voltage, the mediator will be rapidly oxidized. In fact, the mediator will be oxidized so quickly at a sufficiently positive test voltage (i.e., limiting test voltage) that the test current magnitude will be limited by the diffusion of the mediator to the electrode surface (i.e., limiting test current). For an embodiment where first working electrode 12 is a carbon ink and the mediator is ferricyanide, a test voltage of about +400 mV may be sufficient to act as a limiting test voltage. For an embodiment where first working electrode 12 is a carbon ink and the mediator is $Ru^{III}(NH_3)_6$, a test voltage of about +250 mV may be sufficient to act as a limiting test voltage. It will be apparent to one skilled in the art that other mediator and electrode material combinations will require different limiting test voltages.

A test meter that is designed to apply a limiting test voltage can have some variation in the applied test voltage without affecting the magnitude of the limiting test current. It is desirable for a test meter to apply a limiting test voltage because the test meter can be constructed with relatively inexpensive electronic components because it is not necessary to tightly control the test voltage. In summary, a test meter which applies a limiting test voltage can robustly measure a glucose concentration in an accurate and precise manner using low cost components.

Figure 6:
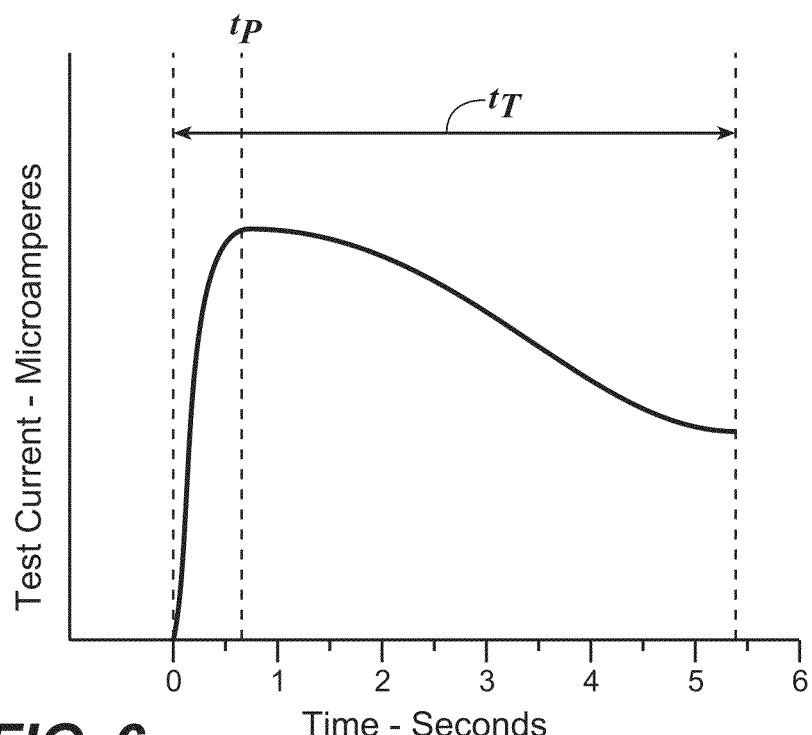
FIG. 6 is a graph illustrating a test current which results from the applied test voltage of FIG. 5 when a blood sample is applied to the test strip of FIG. 1.

FIG. 6 is a chart showing the test current generated by test strip 100 during test time interval $t_T$. In general, the test current increases rapidly when test strip 100 is initially wetted with the physiological fluid and then forms a peak at a maximum peak time $t_p$. After the peak maximum, the test current gradually decreases. As discussed earlier, the overall magnitude of the test currents will decrease with increasing hematocrit levels. In addition, the overall magnitude of the test currents will increase with increasing glucose concentration. The maximum peak time $t_p$ is expected to increase with increasing hematocrit levels, causing the overall shape of the test current as a function of time to be changed by the hematocrit level. In summary, both glucose concentration and hematocrit level will have an effect on the magnitude of the test currents and shape of the test current curve during the test time interval making it difficult to measure the glucose concentration accurately in a manner independent of hematocrit.

To help define a new algorithm which uses a larger proportion of the measured test current, a model equation was developed for predicting the test current values measured from a test strip. One of the purposes for creating the model equation was to define the input variables which affect the magnitude of the test current and the mathematical relationship between the input variables. In one model equation embodiment, such input variables may include hematocrit h, glucose concentration G, and time t. By mathematically defining the effect of hematocrit on the magnitude of the test current, it is possible to tailor a correction function to remove the effect of hematocrit.

To develop the model equation for a particular type of test strip (e.g., test strip 100 as illustrated in FIGS. 1 and 2), an experiment may be performed using several test strip lots and testing blood samples having a wide range of known glucose concentrations and hematocrit levels. A test strip lot is a batch of strips that provide test currents having substantially the same magnitude and shape when tested with multiple blood samples having the same glucose concentration and hematocrit level. Typically, test strips made during a single run or day will be segregated into one lot.

The blood samples used to perform these tests described above may have a hematocrit level ranging from, for example, about 20% to about 70% and a plasma glucose concentration ranging from, for example, about 40 mg/dL to about 730 mg/dL. For a blood sample having a particular glucose concentration and hematocrit level, multiple test strips from the same lot may be tested and the results recorded. As an example, eight test strips from each lot may be tested using blood having a pre-determined glucose concentration and hematocrit level. The test may then be repeated for several more blood samples that have a range of glucose concentrations and hematocrit levels.

After collecting the actual test current curves for a plurality of test strip lots which were tested with a plurality of blood samples, a model equation may be developed for predicting the magnitude of an average test current curve based on a particular glucose concentration and hematocrit level with a particular type of test strip (e.g., test strip 100 of FIG. 1). For example, Equation 4 shows a model equation for predicting the test current value I as a function of hematocrit h, glucose G, and time t for a particular type of test strip. An equation such as, for example, Equation 4 may be empirically derived from the previously measured test current values collected for several test strip lots which were tested with multiple variations of glucose concentration and hematocrit levels.

$$I(h,G,t)=[1-c(t)h][a(t)+b(t)G] \quad \text{Eq. 4}$$

The term $I(h,G,t)$ is the estimated test current value in units of microamperes; h is the hematocrit level in units of a fraction; G is the glucose concentration in units of mg/dL; t is the time in units of seconds; $c(t)$ is the hematocrit sensitivity as a function of time; $a(t)$ is the background sensitivity as a function of time; and $b(t)$ is the glucose sensitivity as a function of time.

Figure 7:
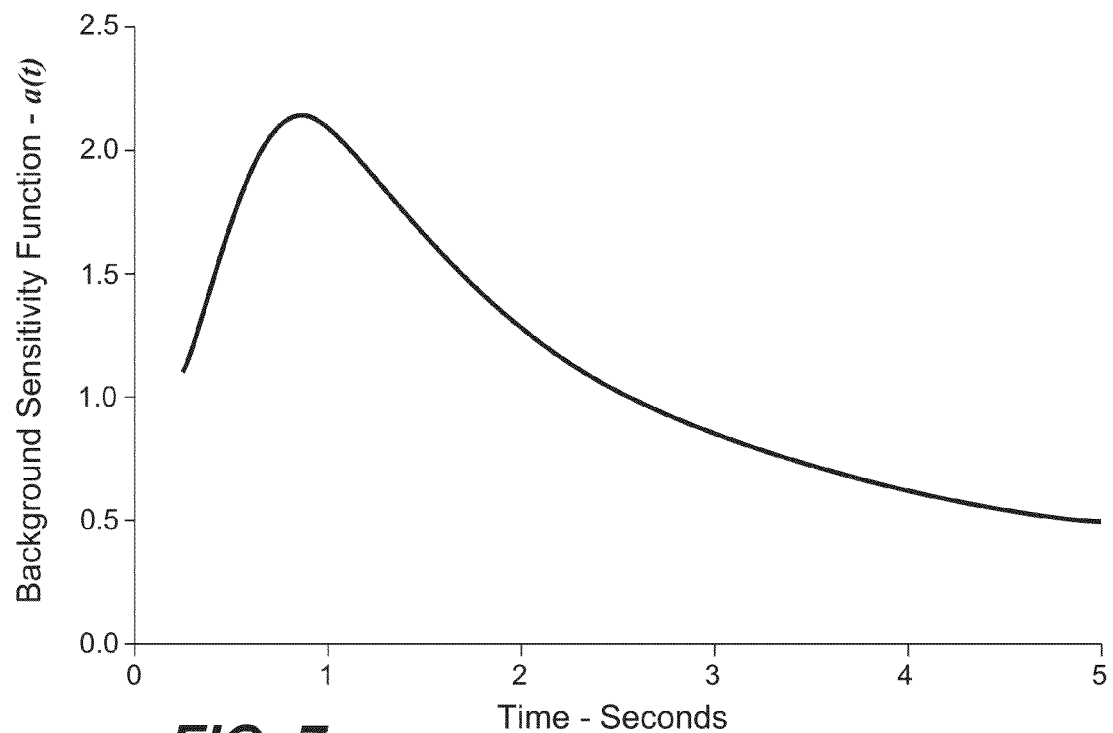
FIG. 7 is a graph showing an empirically derived background sensitivity function a(t) which can be used for defining the correction function q(t) so that the hematocrit error function S of Equation 11 is minimized or reduced.
Figure 8:
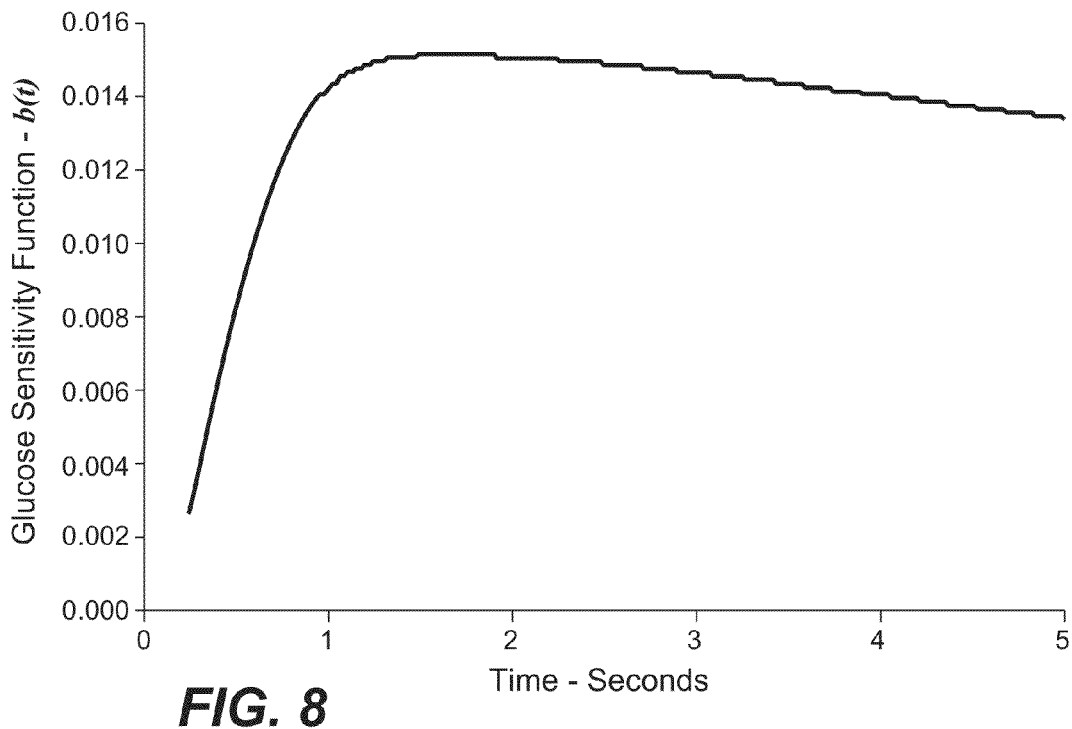
FIG. 8 is a graph showing an empirically derived glucose sensitivity function b(t) which can be used for defining the correction function q(t) so that the hematocrit error function S of Equation 11 is minimized or reduced.
Figure 9:
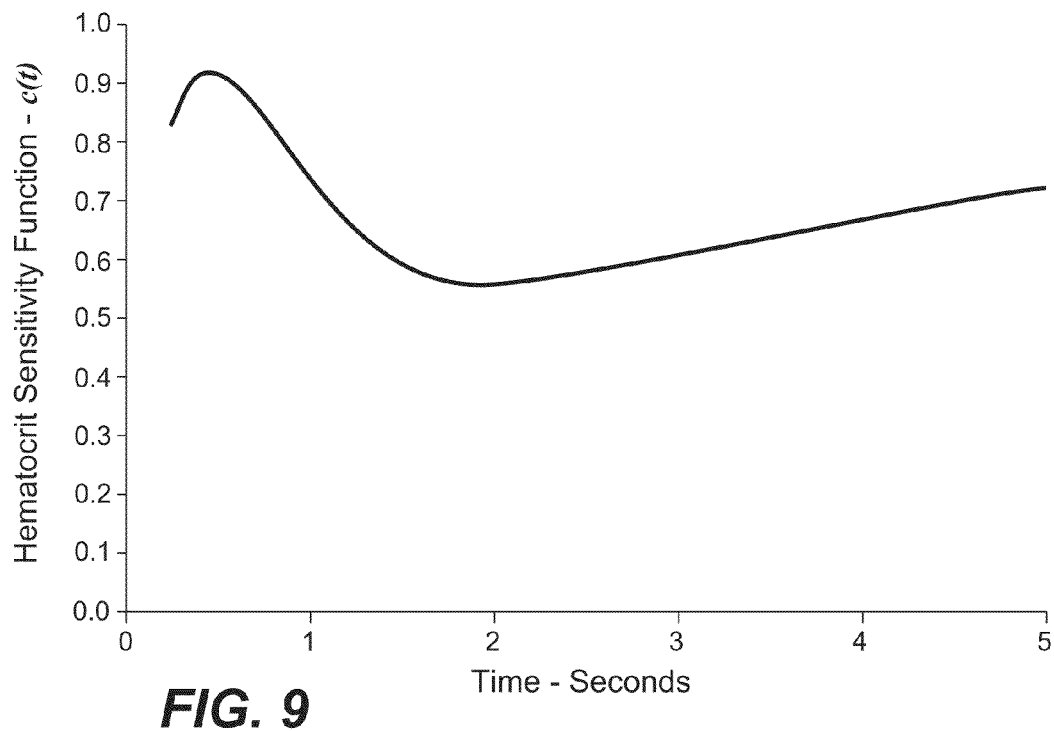
FIG. 9 is a graph showing an empirically derived hematocrit sensitivity function c(t) which can be used for defining the correction function q(t) so that the hematocrit error function S of Equation 11 is minimized or reduced.

Once a model equation format has been selected, the model equation may be optimized to effectively predict the measured test currents for a particular type of test strip. For example, in Equation 4, the three functions $a(t)$, $b(t)$, and $c(t)$ may be derived using the above described data where actual test strip current values from several test strip lots which were tested with several blood samples having a range of known glucose concentrations and hematocrit levels. The three functions ($a(t)$, $b(t)$, and $c(t)$) may each be defined as a series of best fit values using non-linear regression for each individual test time point as shown in FIGS. 7 to 9.

After defining the best fit values for the three functions $a(t)$, $b(t)$, and $c(t)$ using a particular group of test strip lots, Equation 4 may then be verified by testing a different group of test strip lots using several blood samples having known glucose concentrations and hematocrit levels as described above. For example, the measured test current values for the different group of test strip lots may be shown to substantially agree with the estimated test current values using Equation 4.

A model equation (Equation 4) may estimate the average test current response for a particular type of test strip when the hematocrit level, glucose concentration, and time are known. Because the model equation may not estimate the test current response in a sufficiently accurate manner over the entire test time interval $t_T$, a portion of the test time interval $t_T$ may be defined where the model equation is sufficiently accurate. For instance, the model equation may estimate the test current within about 80% or greater of the measured test current for a time interval between about 0.1 seconds to about 5 seconds. Thus, in such a scenario, the estimated test current values, using Equation 4, should only be calculated for test times between about 0.1 seconds and about 5 seconds when developing an algorithm to remove the effects of hematocrit. For obvious reasons, if Equation 4 cannot accurately estimate the magnitude of the test current values for a particular time interval, then it would not make sense to use test currents in that time interval in an algorithm for removing the effects of hematocrit. For purposes of developing an effective algorithm for reducing the effects of hematocrit, it is desirable for the model equation to estimate the test current response in a sufficiently accurate manner over substantially all of the test time interval $t_T$.

Once the test current values have been mathematically modeled in a way that accounts for the hematocrit contribution as a function of time (see $c(t)$), it is now possible to empirically determine a correction function $q(t)$ which may remove or attenuate the contribution of hematocrit. Thus, the estimated test current $I(h,G,t)$ may be multiplied by a correction function $q(t)$ for removing the effects of the hematocrit. In an embodiment of this invention, Equation 5 shows that the correction function $q(t)$ may be multiplied by a test current function $I(h,G,t)$ to give an analyte correlation function $y(t)$.

$$y(t)=I(h,G,t)q(t) \quad \text{Eq. 5}$$

Note that the calculation of the analyte correlation function $y(t)$ is an intermediate step used for the calculation of the analyte correlation value (Y) as shown in Equation 6. The analyte correlation function $y(t)$ may be integrated over a pre-determined interval where the model equation is capable of estimating the test current values in an accurate manner. For example, the pre-determined time interval may be between about 0.1 seconds to about 5 seconds to yield an analyte correlation value (Y) as shown in Equation 6.

$$Y=\int y(t)dt=\int I(t)q(t)dt \quad \text{Eq. 6}$$

The analyte correlation value (Y) is a number that is proportional to an accurate glucose concentration with a reduced hematocrit effect. For example, a glucose concentration may be calculated by subtracting a background value from the analyte correlation value (Y) and then dividing by a calibration slope. The following sections will first describe the correction function $q(t)$ in more detail, and then, secondly, describe a hematocrit error function S and its use for defining the terms within the correction function $q(t)$.

In one embodiment of this invention, $q(t)$ may be in the form of a step function having an amplitude of either +1 or -1. In another embodiment of this invention, $q(t)$ may be in the form of a step function having an amplitude of either +1, 0, or -1. For example, $q(t)$ may be +1 for a first pre-determined time interval and -1 for a second predetermined time interval (see FIG. 11). It is also possible that $q(t)$ may be -1 for a first pre-determined time interval and +1 for a second predetermined time interval. Further, it is also possible that a third pre-determined time interval or more pre-determined time intervals may be used to define $q(t)$ (i.e., fourth, fifth, sixth, etc.). This invention should not be limited to only +1, 0, or -1 in that it should obvious to one skilled in the art that other amplitudes, scaled to appropriate values, could be used as well. However, there is an advantage in using only +1, 0, or -1 because it simplifies the amount of microprocessor power needed to perform the calculation. If the cost of microprocessor power is not an issue or if there is readily available source of microprocessor power, then values other than +1 or −1 may be used.

In one embodiment of this invention, the analyte correlation value (Y) may be defined by Equation 7 which uses two pre-determined time intervals, $$Y = \sum_{t=t_{F1}}^{t_{L1}} I(h, G, t)q(t) + \sum_{t=t_{F2}}^{t_{L2}} I(h, G, t)q(t) \quad \text{Eq. 7}$$

where $t_{F1}$ is a starting point of a first pre-determined time interval; $t_{L1}$ is an ending point of a first pre-determined time interval; $t_{F2}$ is a starting point of a second pre-determined time interval; $t_{L2}$ is an ending point of a second pre-determined time interval; and q(t) is a correction function, where in one embodiment of the invention, the correction function is +1 between the starting point $t_{F1}$ and the ending point $t_{L1}$ for the first pre-determined time interval, and −1 between the starting point $t_{F2}$ and the ending point $t_{L2}$ for the second pre-determined time interval.

In another embodiment of this invention, analyte correlation value (Y) may be defined by Equation 8, which uses three pre-determined time intervals.

$$Y = \sum_{t=t_{F1}}^{t_{L1}} I(h, G, t)q(t) + \sum_{t=t_{F2}}^{t_{L2}} I(h, G, t)q(t) + \sum_{t=t_{F3}}^{t_{L3}} I(h, G, t)q(t) \quad \text{Eq. 8}$$

Equation 8 is similar to Equation 7 except that there is a third pre-determined time interval where $t_{F3}$ is a starting point of a third pre-determined time interval; $t_{L3}$ is an ending point of a third pre-determined time interval; and q(t) is a correction function, where in one embodiment of the invention, the correction function is +1 between the starting point $t_{F1}$ and the ending point $t_{L1}$ for the first pre-determined time interval, −1 between the starting point $t_{F2}$ and the ending point $t_{L2}$ for the second pre-determined time interval, and +1 between the starting point $t_{F3}$ and the ending point $t_{L3}$ for the third pre-determined time interval (see FIG. 14). The starting and ending points of the first, second, and third pre-determined time intervals (i.e., $t_{F1}$, $t_{L1}$, $t_{F2}$, $t_{L2}$, $t_{F3}$, and $t_{L3}$) and the correction function q(t) are determined and optimized such that the analyte correlation value (Y) has little to no dependence on the hematocrit level in blood.

It should be noted that the exemplary embodiments as described in Equations 7 and 8 also include mathematically equivalent functions that perform substantially the same steps. For the embodiment in which the correction function q(t) is only +1 or −1, the microprocessor can perform an addition step when q(t) is +1 or a subtraction step when q(t) is −1. By performing only addition or subtraction, as opposed to multiplication, the microprocessor does not need the increased functionality required for performing a floating point operation.

A mathematically equivalent embodiment of this invention, which is a method, can be applied to Equations 7 and 8. The embodiment as applied to Equation 7 for determining an analyte concentration may include applying a test voltage between a working electrode and a reference electrode. The test meter may measure a plurality of test currents when blood containing glucose is applied to the test strip. A first portion of the plurality of test currents may be added together over a first pre-determined time interval to form a first total. Next, each test current value within a second portion may be subtracted from the first total to form a second total. A glucose concentration with a reduced effect of hematocrit can now be calculated based on the second total.

Another mathematically equivalent embodiment, which is a method, for performing the function of Equations 7 and 8 uses the distributive law of mathematics which states that the product of a number and the sum of two other numbers (i.e., A×(B+C)) is the same as the sum of the products of the number and each of the original addends (i.e., (A×B)+(A×C)). In an embodiment of this invention, a method for determining an analyte concentration includes applying a test voltage between a working electrode and a reference electrode. The test meter may measure a plurality of test current values when a blood sample containing glucose is applied to the test strip. A first total of the test currents can be calculated over a first pre-determined time interval. Next, the first total is multiplied by a first correction factor. A second total of the test currents can be calculated over a second pre-determined time interval. Next, the second total is multiplied by a second correction factor. The first total and the second total may be summed together to form an aggregate. The aggregate can then be correlated to the analyte concentration. In this embodiment of the invention, the first and second correction factor do not necessarily have to be equal to either +1 or −1.

In an embodiment of this invention, a number of predetermined time intervals and a duration for each of the pre-determined time intervals needs to be calculated for defining the correction function q(t). For simplicity, it would be desirable to use the minimum number of pre-determined time intervals to achieve an algorithm that outputs a sufficiently accurate glucose concentration using a test strip. In one embodiment, it may be initially assumed that the number of pre-determined time intervals is set to two and then the duration of the pre-determined time intervals may be systematically changed until an overall accurate set of glucose concentrations can be outputted. The correction function q(t) may be optimized to the provide accurate glucose concentrations by determining the lowest overall bias of the glucose concentration by comparing the % bias between the glucose concentration found with a test strip and the reference method. If two pre-determined time intervals are not found to make the algorithm sufficiently accurate, then more pre-determined time intervals may be added to the correction function q(t).

The previous sections have described possible embodiments of the correction function q(t). However, a correction function q(t) may need to be optimized such that the effects of hematocrit are reduced. For example, the correction function q(t) in Equation 7 requires that the terms $t_{F1}$, $t_{L1}$, $t_{F2}$, and $t_L$, which are contained within the correction function q(t), be defined such that the effects of hematocrit are reduced. The following will describe a process for deriving a hematocrit error function S based on the model equation (Equation 4) for helping define the terms within the correction function q(t).

As a first part of the process for deriving a hematocrit error function S, Equations 4 and 6 may be combined to form Equation 9.

$$Y = \int y(t)dt = \int [1-c(t)h][a(t)+b(t)G]q(t)dt \quad \text{Eq. 9}$$

Secondly, Equation 9 can then be rearranged to Equation 10 as illustrated below.

$$Y = \int a(t)q(t)dt - h\int a(t)c(t)q(t)dt + G\int b(t)q(t)dt - hG\int b(t)c(t)q(t)dt \quad \text{Eq. 10}$$

Note that only the second and fourth integral terms of Equation 10 have the hematocrit term. Thus, as a third part of this process, the hematocrit error function S incorporates the second and fourth integral terms which may be minimized together to be about zero or the smallest value possible, as shown in Equation 11, so as to reduce the effects of hematocrit. Equation 11 may then be used for determining the correction function q(t) that reduces the effects of hematocrit.

$$S = [\int a(t)c(t)q(t)dt]^2 + [\int b(t)c(t)q(t)dt]^2 \approx 0 \quad \text{Eq. 11}$$

As described earlier, the functions a(t), b(t), and c(t) were empirically determined using the measured test currents from a large number of test strip. Therefore, based on the previously tested test strips used to define a(t), b(t), and c(t), the correction function q(t) can be defined in terms of the number of pre-determined time intervals, and also in regards to the starting and ending points for the predetermined time intervals.

Figure 10:
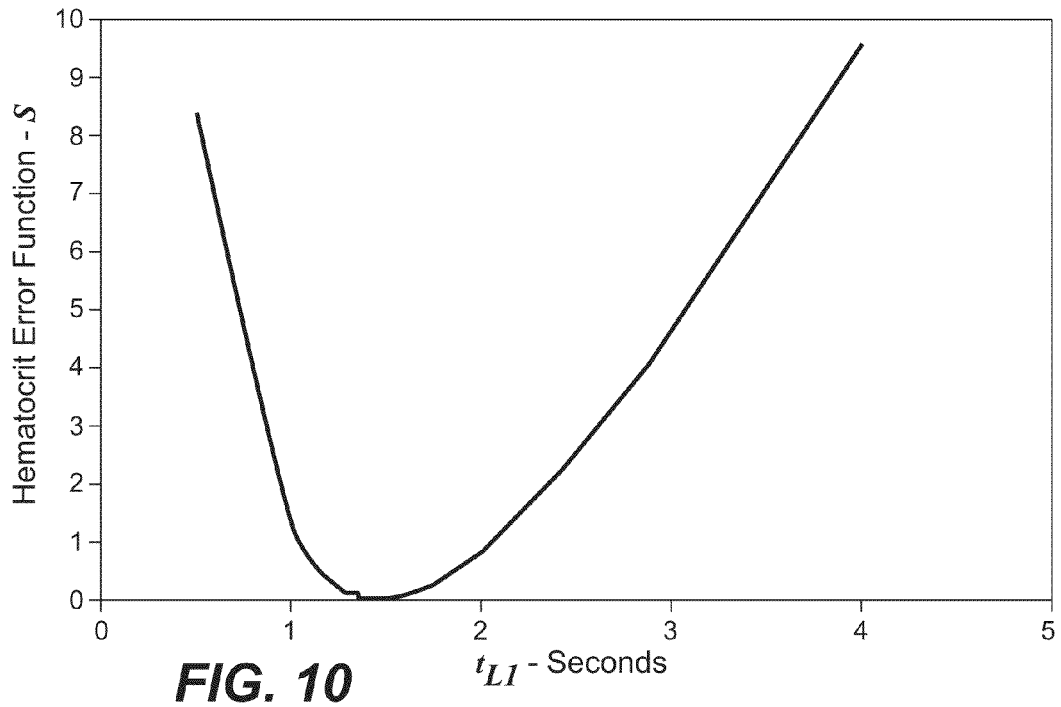
FIG. 10 is a graph of a hematocrit error function S based on a(t), b(t), and c(t) for calculating an ending point of a first pre-determined time interval $t_{L1}$ for a correction function q(t) having two pre-determined time intervals.

As a first embodiment for using Equation 11, it can be assumed that q(t) has two pre-determined time intervals. A minimization of S can be performed by varying the ending point of the first pre-determined time interval $t_{L1}$ as illustrated in FIG. 10. Note that in this case, the ending point of the first pre-determined time interval $t_{L1}$, also coincides with the starting point of the second pre-determined time interval $t_{F2}$. A local minima was observed showing that the ending point of the first pre-determined time interval $t_{L1}$ should be about 1.5 seconds.

Figure 11:
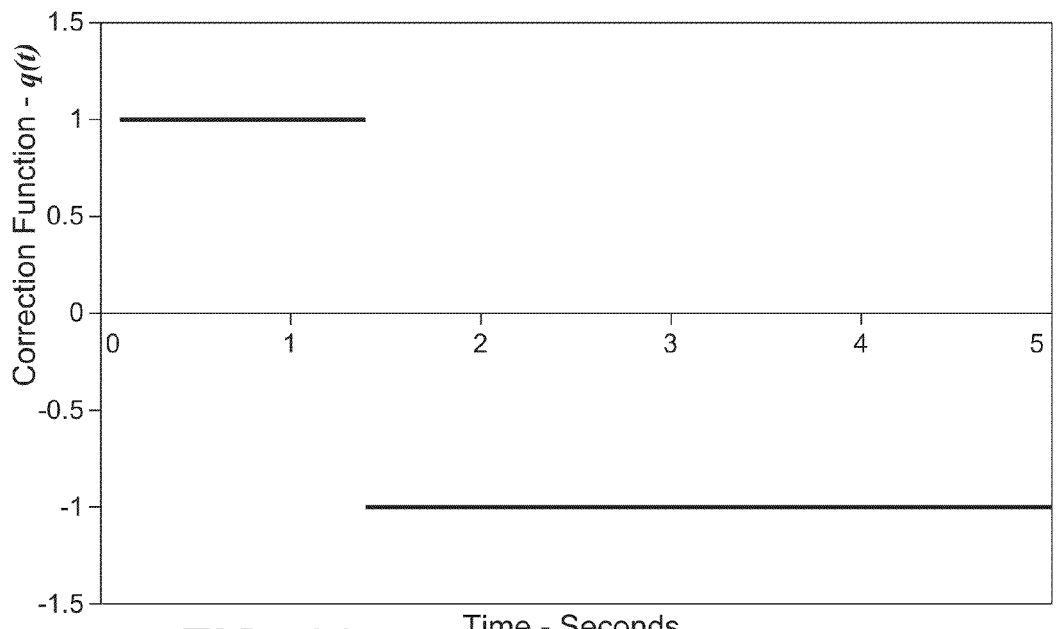
FIG. 11 is a graph showing a correction function q(t) having two pre-determined time intervals for use in Equation 7 for use in removing the effects of hematocrit from a test current curve such as the one shown in FIG. 6.

FIG. 11 shows another embodiment of the correction function q(t) which has two pre-determined time intervals. In order to minimize the hematocrit error function S, the first pre-determined time interval was determined to have a starting point $t_{F1}$ at about 0.1 seconds and an ending point $t_{L1}$ at about 1.5 seconds; and the second pre-determined time interval was determined to have a starting point $t_{F2}$ at about 1.5 seconds and an ending point $t_{L2}$ at about 5 seconds. As illustrated in FIG. 11, the correction function is +1 for the first pre-determined time interval and −1 for the second pre-determined time interval.

The following describes a method in which an algorithm is evaluated for accuracy such as, for example, reducing the effects of hematocrit. Several test strips 100 were tested with test meter 200 using the test voltage as illustrated in FIG. 5. For each test strip 100, a test current was measured over the test time interval $t_T$ and saved to a memory portion of test meter 200. The blood samples tested had a hematocrit level ranging from about 20% to about 70% and a glucose concentration ranging from about 40 mg/dL to 750 mg/dL. The test current transients were then processed using an algorithm to covert the test transient values to a glucose concentration.

A bias to a reference method can be used to compare the algorithm using the "end current" value or the correction function q(t). The "end current" values and analyte correlation values (Y) can be converted into a glucose concentration using a simple slope and intercept values which are assigned to the test strip lot. The resulting glucose concentrations can then be compared to a reference method to calculate a bias.

The accuracy of a glucose concentration measurement performed with a test strip may be evaluated as a % bias with respect to a concentration measured with a standard laboratory reference instrument (e.g., Yellow Springs Glucose Analyzer). Equation 12 shows how a % bias can be determined.

$$\% \text{ bias} = \left[ \frac{[G]_{ts} - [G]_{ref}}{[G]_{ref}} \right] \times 100 \quad \text{Eq. 12}$$

The term $[G]_{ts}$ is the glucose concentration measured with a test strip and $[G]_{ref}$ is the glucose concentration measured with a standard laboratory reference instrument. When testing a sufficiently large number of test strips, a system may be considered "accurate" if it has greater than or equal to 95% of the test strip measurements within a preferable range of about +/−20% bias to the reference measurement value, more preferably the range may be about +/−10% bias to the reference measurement value, and yet more preferably the range may be about +/−5% bias to the reference measurement value. Based on the data used in FIGS. 12, 13, and 15, the variance in biases was found to increase with increasing glucose concentration (data not shown). Therefore, a mixed unit approach was used to evaluate accuracy. For example, glucose concentrations less than or equal to 100 mg/dL were evaluated as an absolute bias, as illustrated in Equation 13, and glucose concentrations greater than 100 mg/dL were evaluated as a % bias, as illustrated in Equation 12.

$$\text{absolute bias} = [G]_{ts} - [G]_{ref} \quad \text{Eq. 13}$$

Figure 12:
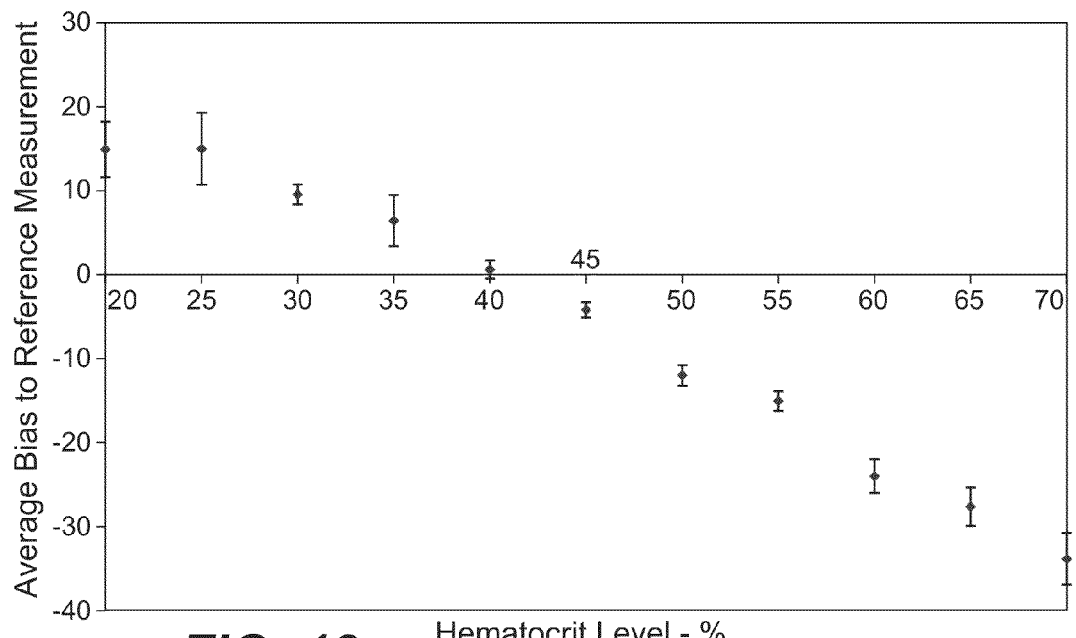
FIG. 12 is graph showing the average bias of a test strip measurement to a reference measurement as a function of hematocrit level using an "end current" algorithm where various blood samples having a range of glucose concentrations and hematocrit levels were tested.
Figure 13:
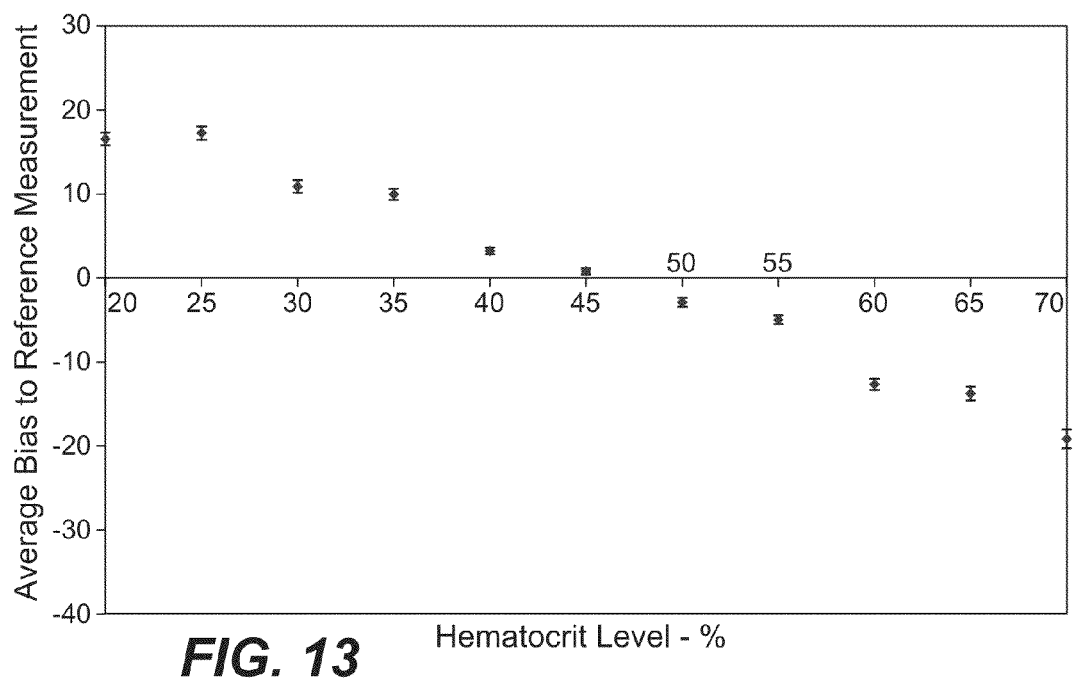
FIG. 13 is graph showing the average bias of a test strip measurement, using the algorithm of Equation 7, to a reference measurement, as a function of hematocrit level, using two pre-determined time intervals, where various blood samples having a range of glucose concentrations and hematocrit levels were tested according to an embodiment of this invention.

FIG. 12 shows the overall bias to the reference method, as a function of hematocrit, when using the "end current" algorithm. In FIG. 12, the test strip biases tested over a range of glucose concentrations were averaged together for a given hematocrit level. FIG. 12 shows that there is a substantial linear dependence on hematocrit where the bias becomes increasingly negative as the hematocrit increases. In FIG. 12, the bias ranged from about +15% at 20% hematocrit to about −30% at 70% hematocrit. FIG. 13 shows the overall bias to the reference method as a function of hematocrit, when using the correction function q(t) that has two pre-determined time intervals. Although the bias in FIG. 13 still shows a dependence on hematocrit level, it is substantially less than the hematocrit dependence as illustrated in FIG. 12. In FIG. 13, the bias ranges from about +15% at 20% hematocrit to about −20% at 70% hematocrit. Thus, the use of correction function q(t) as illustrated in FIG. 11 is an improvement over the prior art "end current" algorithm.

Figure 14:
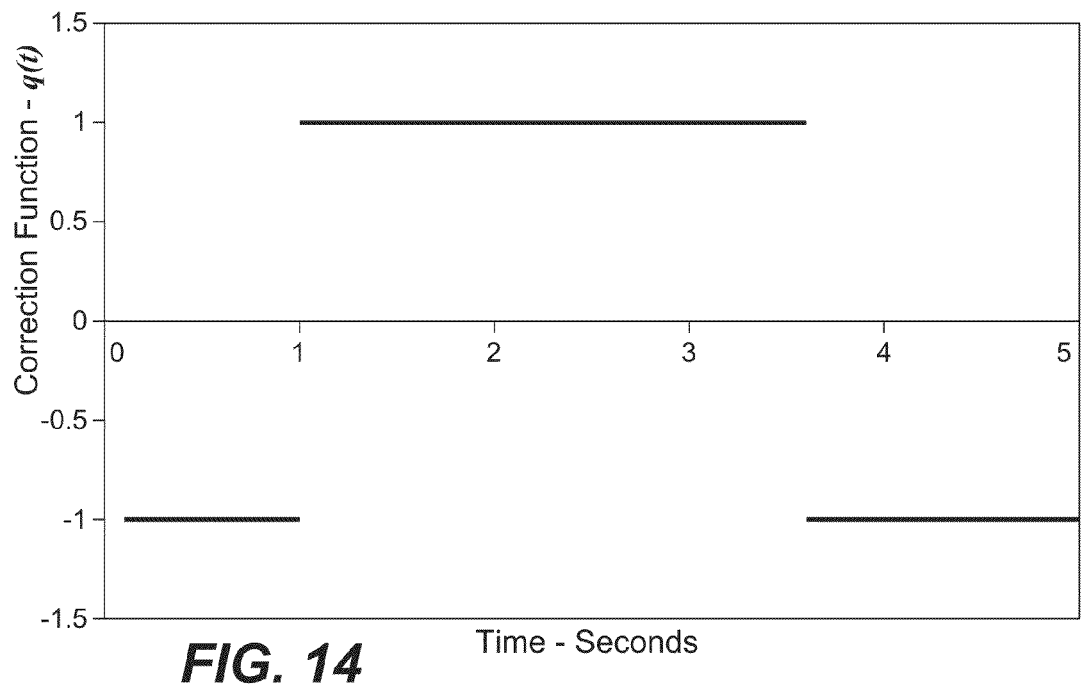
FIG. 14 is a graph showing a correction function q(t) having three pre-determined time intervals for use in Equation 8 for removing the effects of hematocrit from a test current curve such as the one shown in FIG. 6.

In an embodiment of this invention, the correction function q(t) can be adapted to have three pre-determined time intervals instead of only two pre-determined time intervals to further improve the hematocrit correction. FIG. 14 shows an exemplary embodiment of the correction function q(t) which has three pre-determined time intervals. The duration of each of three pre-determined time intervals were optimized to minimize the overall effect of hematocrit. In order to minimize the hematocrit error function S (see Equation 11), the first pre-determined time interval was determined to have a starting point $t_{F1}$ at about 0.1 seconds and an ending point $t_{L1}$ at about 1 second; the second pre-determined time interval was determined to have a starting point $t_{F2}$ at about 1 second and an ending point $t_{L2}$ at about 3.6 seconds; and the third pre-determined time interval was determined to have a starting point $t_{F3}$ at about 3.6 second and an ending point $t_{L3}$ at about 5 seconds. As illustrated in FIG. 14, the correction function is −1 for the first pre-determined time interval, +1 for the second pre-determined time interval, and −1 for the third pre-determined time interval.

Figure 15:
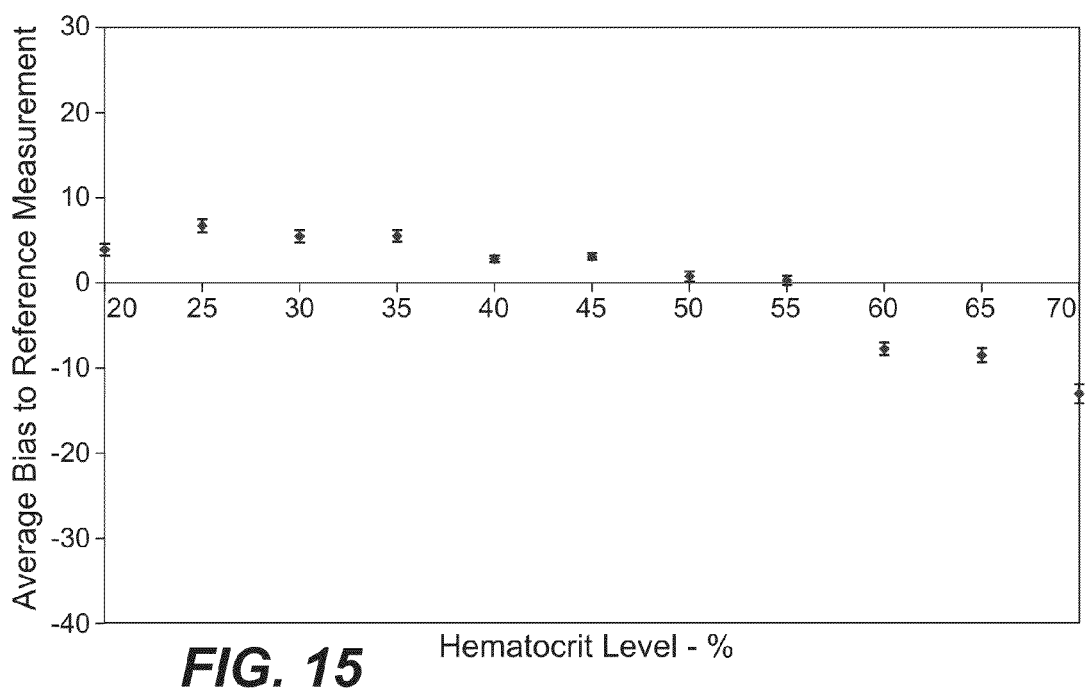
FIG. 15 is a graph showing the average bias of a test strip measurement, using the algorithm of Equation 8, to a reference measurement as a function of hematocrit level, using three pre-determined time intervals, where various blood samples having a range of glucose concentrations and hematocrit levels were tested according to an embodiment of this invention.

FIG. 15 shows the overall bias to the reference method as a function of hematocrit when using the correction function q(t) having three pre-determined time intervals. As can be seen in FIG. 15, the bias ranges from about +7% to about −13% over the range of hematocrit levels tested. Thus, the correction function q(t), as illustrated in FIG. 14, using three pre-determined time intervals is an improvement over the correction function q(t), as illustrated in FIG. 13 which uses only two pre-determined time intervals.

It should be obvious to one skilled in the art that more than three pre-determined time intervals can be used in the correction function q(t) for reducing the effects of hematocrit. However, there is a possibility of overcorrecting the test current and making the algorithm less accurate if too many pre-determined time intervals are implemented.

In an alternative embodiment to this invention, the correction function q(t) can be in the form of a Walsh-Hadamard transform (WHT) function. A WHT function may be a square wave having a pre-determined frequency and a pre-determined amplitude. For example, the correction function q(t) in Equation 7 can be in the form of a WHT function $f_2(t)$ if the first pre-determined time interval is equal to the second pre-determined time interval as illustrated in FIG. 16. The subscript 2 represents the number of pre-determined time intervals. For a WHT function $f_2(t)$, the duration of the first pre-determined time interval must be about equal to the duration of the second pre-determined time interval.

As another example, the correction function q(t) in Equation 8 may be in the form of a WHT function $f_3(t)$ if a sum of the duration of the first pre-determined time interval and the third pre-determined time interval equals the duration of the second pre-determined time interval as illustrated in FIG. 17. In other words, the duration of the first pre-determined time interval must be equal to the duration of the third pre-determined time interval; and the duration of the second pre-determined time interval must be equal to two times the duration of either the first or third pre-determined time interval.

A WHT average value $C_x$ may be calculated for determining a glucose concentration as illustrated by Equation 14.

$$C_x = \frac{1}{z}\sum_{v=1}^{z} I(h, G, t_v) f_x(t_v)$$ Eq. 14

The WHT average value $C_x$ is calculated from a WHT function $f_x(t_v)$ having x pre-determined time intervals. The term $t_v$ represents a time increment in which a magnitude of a test current is calculated. The term z represents the total number of time increments used for calculating the WHT average value. FIGS. 16 to 20 are examples of WHT functions where the number of pre-determined time intervals are 2, 3, 4, 5, or 9.

In an embodiment of this invention, a plurality of WHT average values $C_x$ can be used to calculate a glucose concentration $[G]_{ts}$ as shown in Equation 15 with a reduced effect of hematocrit.

$$[G]_{ts} = \beta_0 + \sum_{x=1}^{d} \beta_x C_x$$ Eq. 15

The term $\beta_0$ is a background calibration term and $\beta_x$ is another calibration term which allows a weighting factor to be used for tailoring a plurality of WHT average values $C_x$ for the purpose of reducing the effects of hematocrit. The term d is the number of WHT functions which are used to calculate the glucose concentration. A plurality of calibration terms ($\beta_0$ and $\beta_x$'s) can be derived by testing a plurality of blood samples having a range of glucose concentrations and hematocrit levels with a particular lot of test strips. The test currents measured with the test strips from the strip lot may be used for determining the optimized plurality of calibration terms ($\beta_0$ and $\beta_x$'s) which minimizes the overall bias with respect to a standardized reference glucose measurement. In summary, the WHT functions provide a scalable tool for reducing the effects of hematocrit by using a sufficient number of WHT average values $C_x$'s and calibration terms ($\beta_0$ and $\beta_x$'s).

In an alternative embodiment of the invention, the method for determining an accurate glucose concentration with a reduced effect from hematocrit may be further improved by determining a maximum peak time $t_p$ for defining the duration of the first pre-determined time interval. In contrast to the previously described embodiments, the first pre-determined time interval is not fixed, but instead is adaptive where it could possibly change for each test strip that is tested.

For example, test meter 200 may calculate the maximum peak time $t_p$ for a test strip which is tested with blood. In this embodiment, memory 210 and microprocessor 212 of test meter 200 can calculate a maximum peak time $t_p$ by finding the largest magnitude test current value collected over the test time interval $t_T$. In another embodiment, the memory and microprocessor of test meter 200 can calculate a maximum peak time $t_p$ by finding a local maxima. After determining maximum peak time $t_p$, Equation 16 can be used to determine a last point of the first pre-determined time interval $t_{L1}$.

$$t_{L1} = t_p \times \omega$$ Eq. 16

The term $\omega$ is another calibration term which can be used to calibrate a particular lot of test strips. In an embodiment of this invention $\omega$ may be less than one and greater than about 0.5. It should be noted that by defining $\omega$ to be less than one, the maximum peak time $t_p$ will not be within the first pre-determined time interval. For example, WHT function $f_3(t_v)$ or $f_4(t_v)$ (see FIGS. 17 and 18) may be modified such that the last point of the first pre-determined time interval is set to $t_{L1}$. In addition, the correction function q(t) may also be modified such that the ending point of the first pre-determined time interval is set to $t_{L1}$ as defined in Equation 16. In summary, the use of the maximum peak time algorithm, as described in Equation 16, can be used to further reduce the effects of hematocrit when used in conjunctions with one of the algorithms previously described in Equations 7, 8, or 15.

In an embodiment of this invention which uses an adaptive pre-determined time interval where there are three pre-determined time intervals, the duration of the second pre-determined time interval can be defined as being equal to about two times the duration of the first pre-determined time interval. In addition, the duration of the first pre-determined time interval may be about equal to the duration of the third pre-determined time interval. In this embodiment, the test time interval $t_T$ may vary since the maximum peak time $t_p$ will likely change depending on the hematocrit level in blood. As mentioned earlier, high hematocrit blood causes the maximum peak time $t_p$ to increase and low hematocrit blood causes the maximum peak time $t_p$ to decrease.

Figure 22:
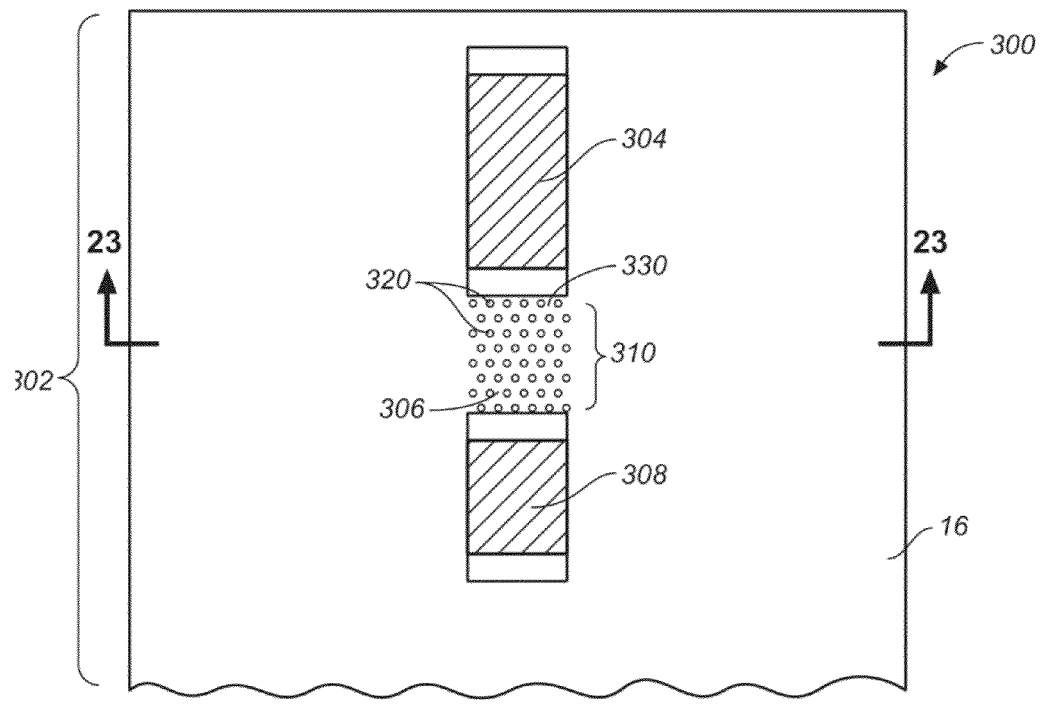
FIG. 22 is a simplified top view of a partial assembly of a test strip embodiment which shows a distal portion of a conductive layer deposed on a substrate having a microelectrode array.

In an alternative embodiment of this invention, a test strip 300 may be used that has a first working electrode 300 in the form of a microelectrode array 310 as illustrated in FIG. 22. In general, microelectrode array 310 will enhance the effects of radial diffusion causing an increase in the measured current density (current per unit area of the working electrode). Radial diffusion refers to the flux of reduced mediator that diffuses to first working electrode 300 in a non-perpendicular manner with respect to a plane of first working electrode 300. In contrast, planar diffusion refers to the flux of reduced mediator that diffuses to first working electrode 300 in an approximately perpendicular manner with respect to a plane of first working electrode 300. As a result of the enhanced radial diffusion, the application of a limiting test voltage to microelectrode array 310 can cause a test current to achieve a non-zero steady-state value which is independent of time. In contrast, the application of a limiting test voltage to a non-microelectrode will result in a test current that approaches zero as time progresses. Because the steady-state value is independent of time for a microelectrode array 310, an effective diffusion coefficient of the mediator in the blood sample may be calculated. In turn, the effective diffusion coefficient can be used as an input into an algorithm for reducing the effects of hematocrit.

A simplified top view of a partial assembly of test strip 300 shows a distal portion 302 of a conductive layer deposed on a substrate 5 as illustrated in FIG. 22. The conductive layer includes a first working electrode 306, a second working electrode 308, and a reference electrode 304. First working electrode 306 is in the form of a microelectrode array 310 which includes a plurality of microelectrodes 320. Many of the layers of test strip 100, as illustrated in FIG. 1, may be used for test strip 300, such as insulation layer 16, reagent layer 22, adhesive layer 60, hydrophilic layer 70, and top layer 80.

Figure 23:
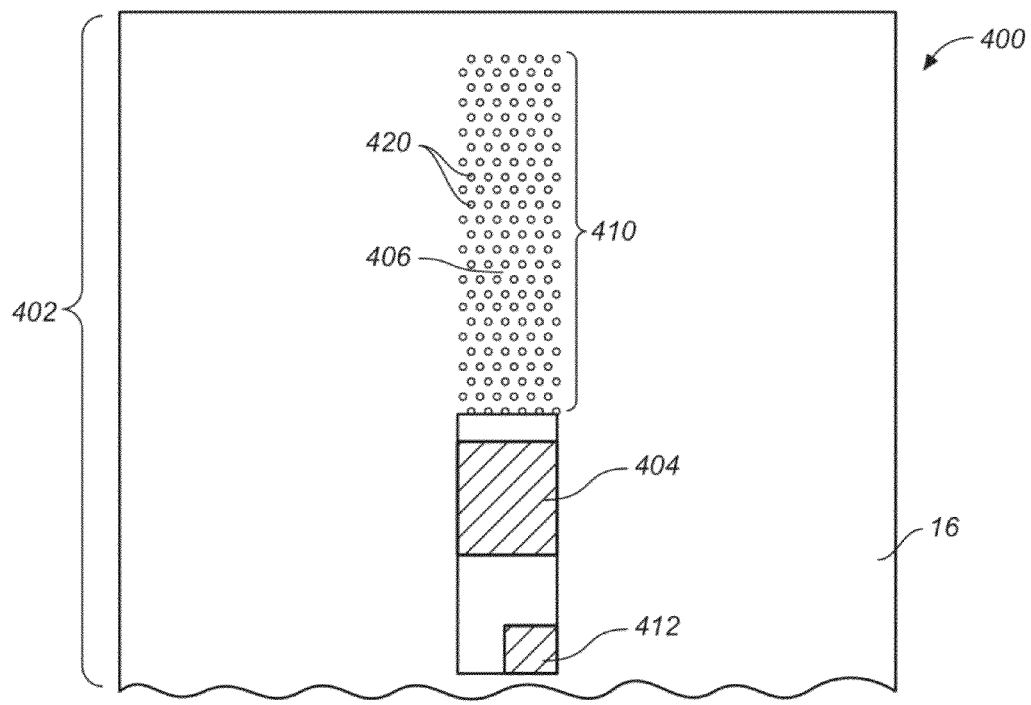
FIG. 23 is a simplified top view of a partial assembly of another test strip embodiment which shows a distal portion of a conductive layer deposed on a substrate having a microelectrode array.

Another embodiment of a microelectrode array is shown as a test strip 400 in FIG. 23. Test strip 400 differs from test strip 300 in that test strip 400 has first working electrode 406 located upstream of reference electrode 404 and also has fill detect electrode 412. The conductive layer includes a first working electrode 406, a fill detect electrode 412, and a reference electrode 404. First working electrode 406 is in the form of a microelectrode array 410 which includes a plurality of microelectrodes 420. Many of the layers of test strip 100, as illustrated in FIG. 1, may be used for test strip 400, such as insulation layer 16, reagent layer 22, adhesive layer 60, hydrophilic layer 70, and top layer 80.

In another embodiment, insulation portion 330 is a separate element from insulation layer 16 of FIG. 1. In this embodiment, insulation portion 330 is disposed on first working electrode 306 in a step separate from the printing of insulation layer 16. Insulation portion 330 may be disposed over and bound to first working electrode 306 by processes such as ultrasonic welding, screen-printing, or through the use of an adhesive. In this embodiment, the holes in insulation portion 330 may be formed before or after adhering insulation portion 330 to first working electrode 306.

In order for microelectrode array 310 to have an enhanced effect due to radial diffusion, insulation portion 330 should have the appropriate dimensions. In one aspect, insulation portion 330 may have a height H which is about 5 microns or less. It is necessary that insulation portion 330 be sufficiently thin so as to allow radial diffusion. If insulation portion 330 was much greater than 5 microns, then insulation portion 330 would interfere with radial diffusion and would actually promote planar diffusion.

Figure 24:
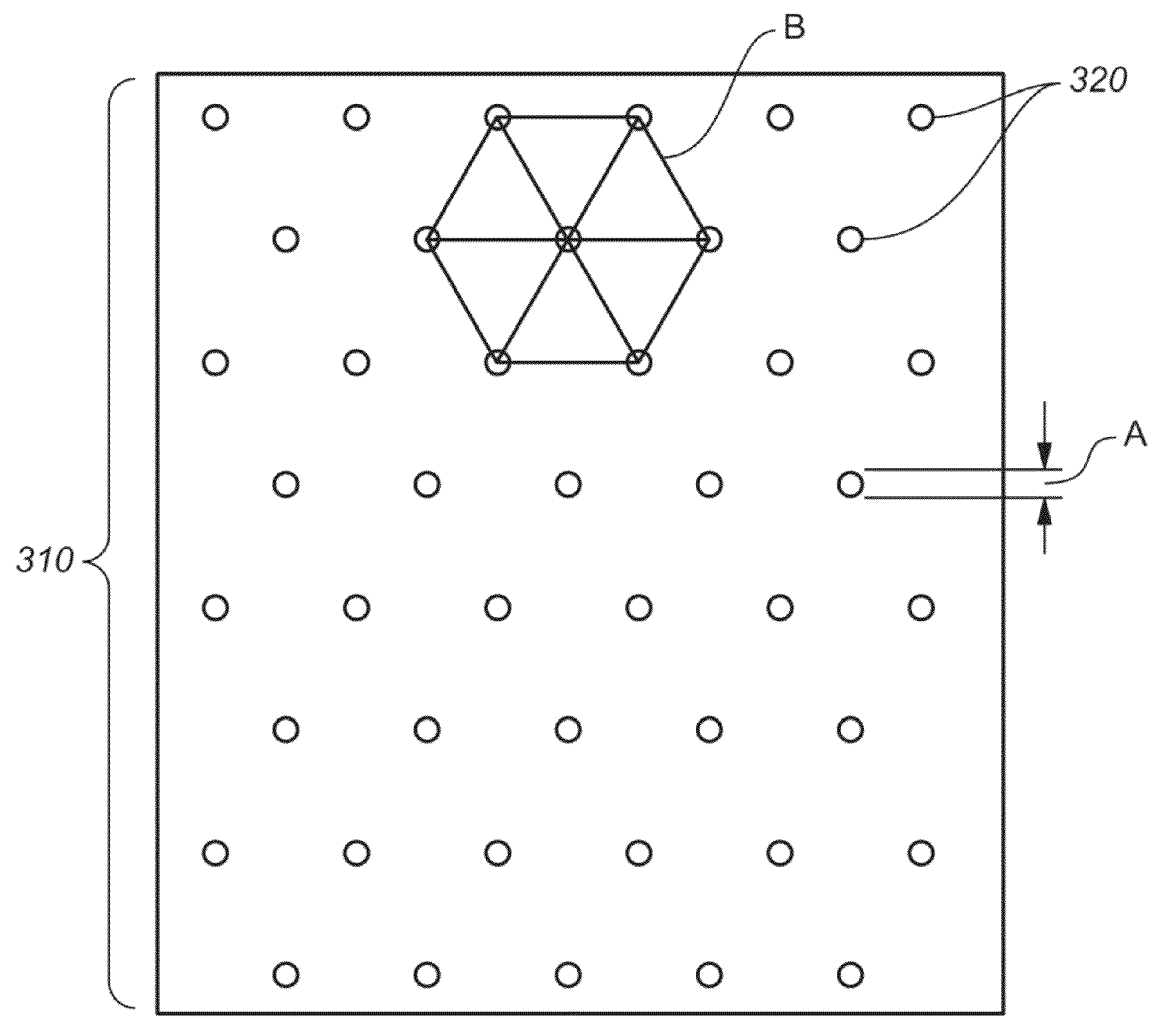
FIG. 24 is a top plan view of the insulation portion of FIG. 22 or 23 having a plurality of openings to expose a plurality of microelectrodes.

In another aspect, each microelectrode 320 should be spaced sufficiently far from each other so as to prevent a first microelectrode from competing with an adjacent second microelectrode for oxidizing mediator. Each microelectrode 320 may be spaced apart with a distance B ranging from about 5 times to about 10 times the diameter of microelectrode 320. In one embodiment as illustrated in FIG. 24, each microelectrode 320 may be evenly spaced throughout insulation portion 330, where a microelectrode may have six neighboring microelectrodes which form a hexagonal shape In yet another aspect, each microelectrode 320 should be sufficiently small such that the proportion of the test current ascribed to radial diffusion is greater than the proportion of the test current ascribed to planar diffusion. Microelectrode 320 may be in the form of a circle having a diameter ranging from about 3 microns to about 20 microns.

In an alternative embodiment of this invention, a test strip 600, as illustrated in FIGS. 33 and 34, may be used that has an integrated lance (i.e., penetration member) that simplifies the process for extracting blood and applying the extracted blood to the test strip. Instead of lancing a user's skin with a lancing device, expressing blood, and dosing the blood to the test strip, the user can now simply launch the test strip with the integrated lance to extract the blood sample followed by the automatic filling of the test strip.

FIGS. 33 and 34 are perspective and side views, respectively, of test strip 600 which includes a penetration member 602, an adhesive layer 614, a reaction area 605, and electrode pads 606. Test strip 600 has a proximal end 610 and a distal end 612. Electrode pads 606 are located at proximal end 610 and are adapted to attaching to a test meter. Penetration member 602 includes a lancet 620 adapted to pierce a user's skin and draw blood into reaction area 605. Penetration member 602 is adhered to test strip 600 with an adhesive layer 614. This adhesive layer can be a heat seal or pressure sensitive adhesive. Lancet 620 includes a lance base 622 that terminates at distal end 612 of assembled test strip 600. Further descriptions of test strips having an integrated lancet are in the aforementioned International Application No. PCT/GB01/05634 and U.S. patent application Ser. No. 10/143,399. In addition, penetration member 602 can be fabricated, for example, by a progressive die-stamping technique, as disclosed in the aforementioned International Application No. PCT/GB01/05634 and U.S. patent application Ser. No. 10/143,399.

In an alternative embodiment of this invention, a test strip may be used that employs a process of laser ablation for improving the accuracy and precision of the measured analyte concentration. The process of laser ablation on a conductive layer allows the edge definition of the electrode area to be better controlled than with other processes such as screen printing. For example, the resolution of screen printing may be limited by the size of the openings in the screen for printing a reagent layer. When using screen printing to define the electrode pattern, an edge of the conductive layer may be jagged because of the granularity caused by the plurality of openings in the screen. In addition, as will be later described, a laser ablated pattern in the conductive layer may be used to substantially define the electrode area without the need of an insulation layer or an adhesive layer.

Figure 21:
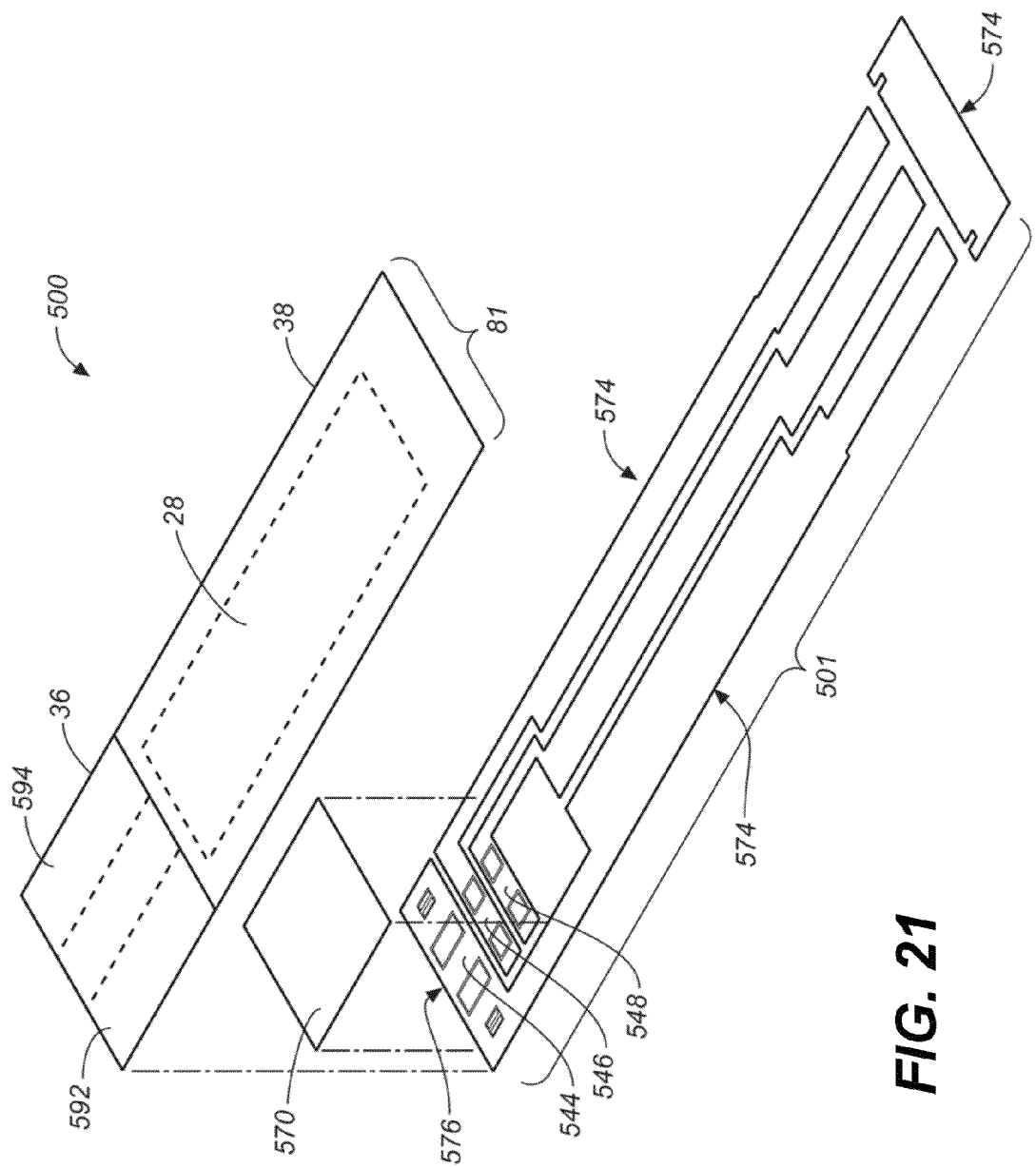
FIG. 21 illustrates a top exploded perspective view of an unassembled test strip which is an embodiment of the present invention

FIG. 21 illustrates a top exploded perspective view of an unassembled test strip 500, which may be used with the proposed algorithms of the exemplary embodiments. Test strip 500 includes a conductive layer 501, a reagent layer 570, and a top tape 81. Test strip 500 has a distal portion 576, a proximal portion 578, and two sides 574, as shown in FIG. 29.

In an embodiment of this invention, the algorithms as described in Equations 7, 8, 15, and 16 may be used with non-microelectrode test strip (100, 500, and 600) and also with microelectrode array test strips (300 and 400). The following will describe another algorithm that may only be applied to microelectrodes and more particularly microelectrode arrays, where the test current achieves a steady-state value because of a higher proportion of radial diffusion.

For a microelectrode array having a plurality of disk shaped microelectrodes where a limiting test voltage is applied, the following equation estimates a ratio of a test current value to a steady-state current value.

$$\frac{I(t)}{I_{ss}} = 1 + \left(\frac{2r_d}{\pi\sqrt{\pi Dt}}\right) \quad \text{Eq. 17}$$

The term $I_{ss}$ is the steady-state current value, $r_d$ is the radius of a disk microelectrode 320 in units of centimeters, D is the effective diffusion coefficient in units of cm$^2$/s. The effective diffusion coefficient D takes into account the diffusion of the mediator in a blood sample having a dissolved reagent layer. In general, the effective diffusion coefficient D should decrease with increasing hematocrit levels. Thus, the effective diffusion coefficient D is dependent on the hematocrit level and can be used in an algorithm for decreasing the effects of hematocrit. The following will describe how to calculate the effective diffusion coefficient D and then apply the effective diffusion coefficient D for calculating a glucose concentration.

Figure 25:
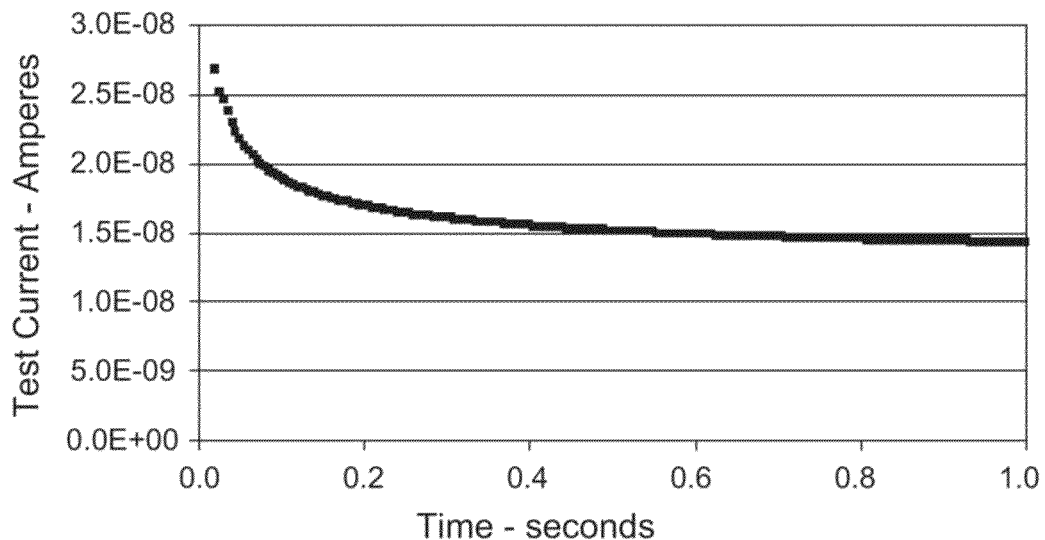
FIG. 25 is a graph illustrating a test current which results from the application of a limiting test voltage when a blood sample is applied to a test strip, of either FIG. 21 or 22, having a microelectrode array.
Figure 26:
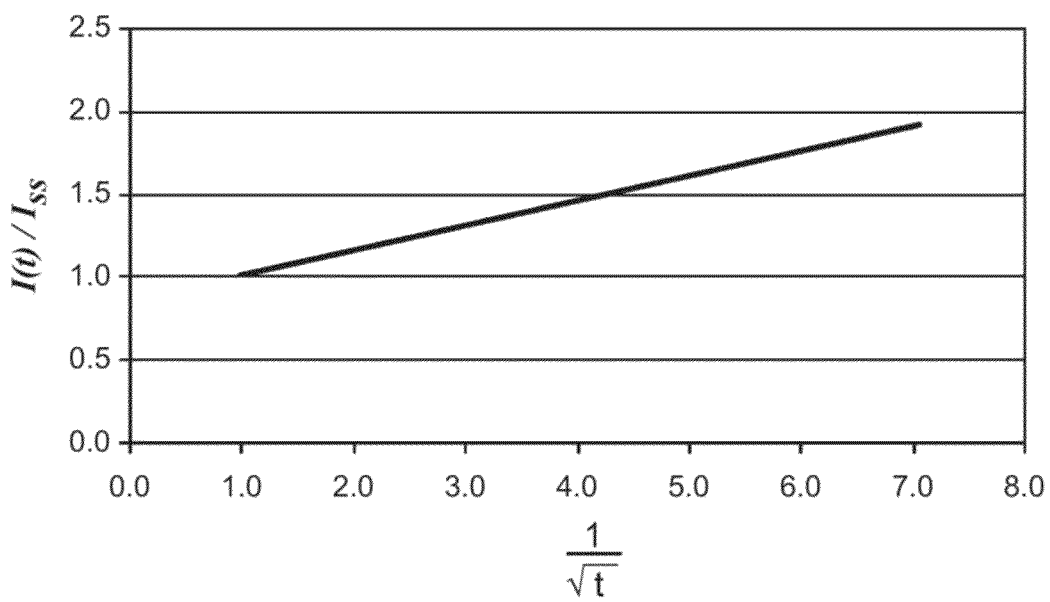
FIG. 26 is a plot of the test current values in FIG. 25 where $$\frac{1}{\sqrt{t}}$$

FIG. 25 is a graph illustrating a test current, which results from the application of a limiting test voltage when a blood sample is applied to a test strip 300 having a microelectrode array. Note that the test current approaches a steady-state current value as time progresses. Using Equation 17, the effective diffusion coefficient D may be estimated by plotting the values $$\frac{I(t)}{I_{ss}}$$

on the y-axis and $$\frac{1}{\sqrt{t}}$$

on the x-axis as illustrated in FIG. 26. The resulting slope from the linear portion of the line may then be calculated and converted into an effective diffusion coefficient D.

In one embodiment, the effective diffusion coefficient D may be used with Equation 18 to estimate the reduced mediator concentration $C_{red}$ (e.g., concentration of $Fe(CN)_6^{4-}$).

$$C_{red} = \frac{I_{ss}}{4nFDr_d} \quad \text{Eq. 18}$$

The terms n is the number of electrons exchanged per reduced mediator molecule and F is Faraday's constant. In turn, $C_{red}$ can be used to estimate the glucose concentration. For example, assuming a linear relationship between $C_{red}$ and glucose concentration, a calibration intercept may be subtracted from $C_{red}$ followed by a division with a calibration slope to yield an estimated glucose concentration. In summary, Equations 17 and 18 allow for glucose concentrations to be calculated with a reduced effect from hematocrit when using microelectrode arrays as illustrated in test strips 300 and 400.

In one embodiment, only one algorithm selected from the Equations 7, 8, 15, 16, 17, and 18 may be used for calculating a glucose concentration. In another embodiment, two or more algorithms may be used together to calculate a glucose concentration based on the same test current values from one working electrode. The two or more glucose concentrations may be averaged together to increase the overall accuracy.

In another embodiment, test strip 300, as illustrated in FIG. 22, may use two working electrodes where a first algorithm uses the test current values from first working electrode 306 and a second algorithm uses the test current values from second working electrode 308. Note that for test strip 300 that first working electrode 306 is in the form of microelectrode array 310. In one embodiment, the first algorithm may be based on Equations 17 and 18, the second embodiment may be based on Equation 8. Therefore, through the use of two separate algorithms, a more accurate glucose concentration may be calculated by averaging together the glucose concentrations from the two separate algorithms.

EXAMPLE

The reagent layer was formulated as an enzyme ink suitable for screen printing as follows. 100 mL of 200 mM aqueous phosphate buffer was adjusted to pH 7. A mixture was formed by adding 5 g of hydroxyethyl cellulose (HEC), 1 g of poly(vinyl pyrrolidone vinyl acetate) (PVP-VA S-630), 0.5 ml of DC 1500 Dow Corning antifoam to 100 mL of phosphate buffer and mixed by homogenization. The mixture was allowed to stand overnight to allow air bubbles to disperse and then used as a stock solution for the formulation of the enzyme ink. Next, 7.5 grams of Cab-o-Sil TS610 was gradually added by hand to the mixture until about 4/5 of the total amount of Cab-o-Sil TS610 had been added. The remainder Cab-o-Sil TS610 was added with mixing by homogenization. The mixture was then rolled for 12 hours. About 18 g of ruthenium hexamine ($[Ru^{III}(NH_3)_6]Cl_3$) was then added and mixed by homogenization until dissolved. Finally, 2.8 g of glucose oxidase enzyme preparation (250 Units/mg) was added and then thoroughly mixed into the solution. The resulting formulation was ready for printing, or could be stored with refrigeration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods within the scope of these claims and their equivalents be covered thereby.

What is claimed is:

1. A method for determining an analyte concentration using a test strip having a working electrode and a reference electrode, the method comprising:
   applying a test voltage between the working electrode and the reference electrode;
   measuring a plurality of test currents with the test meter when a blood sample containing the analyte is applied to the test strip;
   calculating an analyte correlation value (Y) using an equation which is $$Y = \sum_{t=t_{F1}}^{t_{L1}} I(h, G, t)q(t) + \sum_{t=t_{F2}}^{t_{L2}} I(h, G, t)q(t) + \sum_{t=t_{F3}}^{t_{L3}} I(h, G, t)q(t)$$

where $t_{F1}$ is a starting point of a first pre-determined time interval, $t_{L1}$ is an ending point of a first pre-determined time interval, $t_{F2}$ is a starting point of a second predetermined time interval, $t_{L3}$ is an ending point of a second pre-determined time interval, $t_{F3}$ is a starting point of a third pre-determined time interval, $t_{L3}$ ia an ending point of a third pre-determined time interval, I(t) is a current as a function of hematocrit h, glucose G, and time t, q(t) is a correction function of time t.; and calculating the analyte concentration base on the analye correlation value (Y)

wherein the method further comprises the step of calculating the ending point and starting point of the first pre-determined time interval, the second pre-determined time interval, and the third pre-determined time interval $(t_{F1}, t_{L1}, t_{F2}, t_{L2}, t_{F3}, \text{ and } t_{L3})$ using an error minimization function S, wherein the error minimization function S is based on a background sensitivity function a(t), glucose sensitivity function b(t), and a hematocrit sensitivity function c(t), wherein the error minimization function S is $$S=\int [a(t)c(t)q(t)dt]^2+\int [b(t)c(t)q(t)]^2 \approx 0.$$

2. The method of claim 1, wherein a duration of the first pre-determined time interval, the second pre-determined time interval, and the third pre-determined time interval are calculated by minimizing the effect of hematocrit.

3. The method of claim 1, wherein a sum of a duration of the first pre-determined time interval and of the third pre-determined time interval does not equal the second pre-determined time interval.

4. The method of claim 1, wherein a sum of a duration of the first pre-determined time interval and of the third pre-determined time interval equals the second pre-determined time interval.

5. The method of claim 1, wherein the analyte correlation value (Y) is calculated during the test time interval, whereby a microprocessor in the test meter can calculate the analyte concentration faster than if the test meter calculates the analyte correlation value (Y) after the test time interval.

6. The method of claim 1 further comprising the step of:
determining a maximum peak time from the plurality of test current;
determining an ending point of a first pre-determined time interval by multiplying the maximum peak time times a calibration factor.

7. The method of claim 6, wherein the calibration factor ranges from about 0.5 to about less than one.

8. The method of claim 1, wherein a reagent layer is disposed over the working electrode, the reagent layer comprising:
an enzyme;
a ruthenium hexamine mediator; and
a buffer for dissolving the enzyme and the ruthenium hexamine mediator;
wherein the ruthenium hexamine has a concentration range from about 15% to about 20%(weight/volume).

9. The method of claim 8, wherein the enzyme is a material selected from the group consisting of glucose oxidase and glucose dehydrogenase.

10. The method of claim 8, wherein the buffer is a chemical selected from the group consisting of phosphate, citrate, and citraconate.

11. The method of claim 8, wherein the buffer is phosphate and has a pH of about 7.

12. The method of claim 8, wherein the formulation further comprises a filler having hydrophilic and hydrophobic domains.

13. The method of claim 8, wherein the filler comprises silca modified by surface treatment with methyl dichorosilane.

14. The method of claim 8, wherein the formulation is printed on the working electrode via a screen that secures a plurality of interwoven threads, the plurality of interwoven threads defining a plurality of open rectangular spaces for allowing the formulation to pass therethrough, the plurality of interwoven threads having a thread spacing and a thread diameter, wherein the thread spacing ranges from about 90 threads per centimeter to about 120 threads per centimeter and the thread diameter may range from about 30 microns to about 50 microns.

15. The method of claim 1, wherein the working electrode comprises microelectrode array.

16. The method of claim 1, wherein the test strip further comprises an integrated lance.

* * * * *